(12) United States Patent (10) Patent No.: US 9,348,038 B2
Rowlands et al. (45) Date of Patent: May 24, 2016

(54) SYSTEMS AND METHODS FOR RESETTING PHOTOCONDUCTIVE X-RAY IMAGING DETECTORS

(75) Inventors: John Rowlands, Toronto (CA); Giovanni Decrescenzo, Thunder Bay (CA); Chandra Pokhrel, Thunder Bay (CA); Alla Reznik, Thunder Bay (CA)

(73) Assignee: THUNDER BAY REGIONAL INSTITUTE, Thunder Bay, ON (CA)

( * ) Notice: Subject to any disclaimer, the term of this patent is extended or adjusted under 35 U.S.C. 154(b) by 348 days.

(21) Appl. No.: 13/822,891

(22) PCT Filed: Sep. 13, 2011

(86) PCT No.: PCT/CA2011/050556
§ 371 (c)(1),
(2), (4) Date: Apr. 24, 2013

(87) PCT Pub. No.: WO2012/034229
PCT Pub. Date: Mar. 22, 2012

(65) Prior Publication Data
US 2013/0221241 A1 Aug. 29, 2013

Related U.S. Application Data

(60) Provisional application No. 61/382,317, filed on Sep. 13, 2010, provisional application No. 61/382,368, filed on Sep. 13, 2010.

(51) Int. Cl.
*G01T 1/16* (2006.01)
*H04N 5/32* (2006.01)
(Continued)

(52) U.S. Cl.
CPC . *G01T 1/246* (2013.01); *G01T 1/16* (2013.01);
*H01L 31/115* (2013.01); *H04N 5/32* (2013.01);
*H04N 5/3597* (2013.01); *H04N 5/361*
(2013.01); *A61B 6/4208* (2013.01); *A61B 6/583*
(2013.01)

(58) Field of Classification Search
CPC ....................................................... G01T 1/246
See application file for complete search history.

(56) References Cited

U.S. PATENT DOCUMENTS 4,584,482 A 4/1986 Suzuki et al.
4,687,937 A 8/1987 Aagano et al.
(Continued)

OTHER PUBLICATIONS

PCT International Search Report (PCT/CA2011/050556) dated Jan. 19, 2012.

*Primary Examiner* — David Porta
*Assistant Examiner* — Jeremy S Valentiner
(74) *Attorney, Agent, or Firm* — Lynn C. Schumacher; Stephen W. Leonard; Hill & Schumacher

(57) ABSTRACT

Systems and methods of resetting a blocking-type photoconductive imaging detector are provided. In one embodiment, after having obtained an image, the imaging detector may be reset by applying a reversed bias potential difference and illuminating the imaging radiation detector with photoexcitation radiation. The photoexcitation radiation has a wavelength selected to excite mobile charges within the photoconductive layer and a spatial intensity profile related to the measured image for neutralizing the trapped charges in a spatially compensated manner. In another embodiment, a photoionizing beam is directed onto an x-ray light valve having a liquid crystal layer in contact with a photoconductive layer. The beam passes through an optically transmissive surface of the x-ray light valve and photoionizes a species within the liquid crystal layer, generating mobile charged entities that at least partially neutralize charges trapped at the interface, improving the performance of the x-ray light valve when performing subsequent x-ray imaging.

20 Claims, 23 Drawing Sheets

(51) Int. Cl.
  *H04N 5/361*   (2011.01)
  *G01T 1/24*   (2006.01)
  *H04N 5/359*   (2011.01)
  *H01L 31/115*   (2006.01)
  *A61B 6/00*   (2006.01)

(56) References Cited

U.S. PATENT DOCUMENTS

| | | | |
|---|---|---|---|
| 4,786,808 A | 11/1988 | Saito | |
| 5,017,989 A | 5/1991 | Street et al. | |
| 5,233,555 A | 8/1993 | Aonuma | |
| 5,510,626 A | 4/1996 | Nelson et al. | |
| 5,563,421 A | 10/1996 | Lee et al. | |
| 5,657,056 A * | 8/1997 | Izumi | G02F 1/1365 345/176 |
| 5,869,837 A | 2/1999 | Huang | |
| 5,880,798 A * | 3/1999 | Walton | G02F 1/1396 349/117 |
| 5,905,772 A | 5/1999 | Rutten et al. | |
| 6,078,053 A | 6/2000 | Adam et al. | |
| 6,099,750 A | 8/2000 | Simmerer et al. | |
| 6,528,812 B1 | 3/2003 | Leblans et al. | |
| 6,723,995 B2 | 4/2004 | Rougeot | |
| 6,760,405 B2 | 7/2004 | Ruetten et al. | |
| 7,442,952 B2 | 10/2008 | Kato | |
| 7,496,223 B2 | 2/2009 | Spahn | |
| 7,504,650 B2 | 3/2009 | Suzuki | |
| 7,687,792 B2 | 3/2010 | Rowlands et al. | |
| 7,767,973 B2 | 8/2010 | Hornig | |
| 7,869,568 B2 | 1/2011 | Yokoyama et al. | |
| 2002/0080320 A1 * | 6/2002 | Suzuki | G02F 1/133707 349/153 |
| 2002/0085130 A1 | 7/2002 | Sharma | |
| 2003/0073007 A1 * | 4/2003 | Lahrichi | G03H 1/18 430/1 |
| 2003/0076556 A1 * | 4/2003 | VanWiggeren | G02B 5/32 359/3 |
| 2004/0021101 A1 | 2/2004 | Livingston | |
| 2005/0012057 A1 * | 1/2005 | Smith | G01T 1/2016 250/588 |
| 2007/0201616 A1 * | 8/2007 | Rowlands | G02F 1/1354 378/98.2 |
| 2008/0023660 A1 * | 1/2008 | Suzuki | A61B 6/00 250/588 |
| 2008/0054201 A1 | 3/2008 | Bode et al. | |
| 2009/0290050 A1 | 11/2009 | Herrmann et al. | |
| 2010/0327169 A1 | 12/2010 | Korn | |

* cited by examiner

SYSTEMS AND METHODS FOR RESETTING PHOTOCONDUCTIVE X-RAY IMAGING DETECTORS

CROSS-REFERENCE TO RELATED APPLICATION

This application is a National Phase application claiming the benefit of No. PCT/CA2011/050556 filed on Sep. 13, 2011, in English, which further claims priority to U.S. Provisional Application No. 61/382,368, titled "SYSTEM AND METHOD FOR RESETTING OF X-RAY LIGHT VALVE BY PHOTOIONIZATION" and filed on Sep. 13, 2010, the entire contents of which are incorporated herein by reference, and U.S. Provisional Application No. 61/382,317, titled "SYSTEM AND METHOD FOR RESETTING PHOTOCONDUCTIVE RADIATION DETECTOR" and filed on Sep. 13, 2010, the entire contents of which are incorporated herein by reference.

BACKGROUND

This present disclosure relates to x-ray imaging systems and methods, and more particularly the present disclosure relates to systems and methods of resetting photoconductive blocking type imaging detectors and x-ray light valve based imaging detectors.

Solid state photodetectors are used to detect light or other forms of radiation by converting the radiation to electric charge carriers in the form of electron-hole pairs. An electric potential is then applied to suitable electrodes on the detector, causing the charge to drift towards the electrodes from the point of excitation. Amorphous selenium (a-Se) has been used as a photoconductor in many applications including photocopiers, medical imaging systems and high-definition television broadcasting cameras. Because of its advantages over conventional semiconductors such as silicon, it has the potential for use in many advanced applications that involve photodetection.

While some photoconductive detectors provide a current when biased and illuminated, one class of photoconductive radiation detectors employs a blocking layer to trap photoexcited charges near or at an interface between the photoconductor and an insulating layer. After absorbing radiation in a photoconductive layer and collecting and trapping a sufficient amount of charge, the trapped charge may be interrogated to infer the power, intensity, or fluence of the radiation. For example, the trapped charge may be read out electrically or optically, and subsequently processed to determine an image.

One such photoconductive imaging device is the x-ray light valve (XLV), described in U.S. Pat. No. 7,687,792, which provides an electro-optic material (such as a liquid crystal layer) in contact with a photoconductive layer to convert the trapped charge pattern into spatially dependent anisotropy within the electro-optic material, which can in turn be optically interrogated by a readout optical beam. In general, XLVs include a photoconductor for charge generation and transport, a liquid crystal cell for image formulation, and a scanner for digital image readout. XLVs operate by absorbing x-rays in a photoconductor layer to generate local electrostatic charges. This charge builds up at an interface between the photoconductor and a liquid crystal cell, thereby changing the optical properties of the liquid crystal cell.

This scanning approach requires that the optical image be stable without significant decay over a pre-selected period of time (usually on the order of a few minutes) at the photoconductor-modulator interface. Because of the requirement of long lifetime, it becomes important to neutralize the remaining charge at the interface before a new exposure can be made.

Other blocking type photoconductive imaging devices are disclosed in U.S. Pat. Nos. 5,017,989, 5,510,626, 5,869,837 and 6,760,405. U.S. Pat. Nos. 5,017,989, 5,869,837 and 6,760,405 disclose devices in which the signal obtained by a photoconductor (or a photodiode) is capacitively coupled to a readout circuit, while U.S. Pat. No. 5,510,626 teaches a device in which a pixel-sized beam of readout radiation is raster scanned to produce charges that discharge the pixels and provide a readout current.

One significant drawback of blocking-type photoconductive imaging devices is that they must be reset between uses in order to attempt to neutralize the charges trapped at the interface of the photoconductor and the insulating layer. Such charges, if allowed to persist, affect the quality of subsequently detected images, leading to high background, blurring, and low signal-to-noise ratios.

Various methods of resetting blocking-type photoconductive imaging devices have been proposed. One known solution suggested in U.S. Pat. No. 7,687,792 involves illuminating the device with unfiltered white light while shorting the electrodes. Unfortunately, this method typically provides an imperfect neutralization of the residual charge and often merely smears the charge distribution present in the device without providing significant charge neutralization. After illuminating the photoconductive layer and producing electron-hole pairs, some of the trapped charges are neutralized in the photoconductor by recombining with carriers from the excited pairs. However, after a recombination process, one of the members of a given charge pair will still be present, and the dominant transport mechanism of diffusive transport will often result in the retrapping of the charge.

U.S. Pat. Nos. 5,017,989 and 7,687,792 suggest an improved method in which the device is reverse biased under illumination, where the illumination produces electron-hole pairs in the photoconductive layer that drift under the applied field and recombine with trapped charges at the interface. Unfortunately, this method still results in inefficient resetting, particularly in cases in which deep trap states exist at the photoconductor-insulator interface. The inefficient resetting of the device generates imaging artifacts that persist in reducing device performance when performing subsequent imaging.

SUMMARY

Systems and methods of resetting a blocking-type photoconductive imaging detector are provided. In one embodiment, after having obtained an image, the imaging detector may be reset by applying a reversed bias potential difference and illuminating the imaging radiation detector with photoexcitation radiation. The photoexcitation radiation has a wavelength selected to excite mobile charges within the photoconductive layer and a spatial intensity profile related to the measured image for neutralizing the trapped charges in a spatially compensated manner.

In another embodiment, a photoionizing beam is directed onto an x-ray light valve having a liquid crystal layer in contact with a photoconductive layer. The beam passes through an optically transmissive surface of the x-ray light valve and photoionizes a species within the liquid crystal layer, generating mobile charged entities that at least partially neutralize charges trapped at the interface, improving the performance of the x-ray light valve when performing subsequent x-ray imaging.

Accordingly, in one aspect, there is provided a method of erasing a residual image from an x-ray light valve imaging device, the x-ray light valve imaging device including an electro-optic modulator layer and a photoconductive layer, the method comprising the steps of: providing a photoionization radiation source for generating photoionizing radiation with a wavelength suitable for photoionizing a species within the electro-optic modulator layer of the x-ray light valve imaging device; and directing the photoionizing radiation into the electro-optic modulator layer and photoionizing the species within the electro-optic modulator layer; wherein a fluence of the photoionizing radiation is selected to generate a sufficient concentration of mobile charge entities to reduce an effect of trapped charges located at or near an interface of the photoconductive layer.

In another aspect, there is provided a method of obtaining an x-ray image using an x-ray light valve imaging device, wherein the x-ray light valve imaging device includes a liquid crystal layer, a photoconductive layer, and electrodes for applying a potential bias across the liquid crystal layer and the photoconductive layer, wherein an electrode adjacent to the liquid crystal layer is optically transmissive; the method comprising the steps of: a) providing a photoionization radiation source for generating photoionization radiation having a wavelength suitable for photoionizing a species within the liquid crystal layer of the x-ray light valve imaging device; b) applying an initial bias potential between electrodes; c) exposing the x-ray light valve imaging device to x-ray radiation, wherein the x-ray radiation is absorbed in the photoconductive layer and produces charges, and wherein bias potential causes a portion of the charges to drift to and be trapped at or near an interface of the photoconductive layer, and wherein a local electric field is formed within the liquid crystal layer due to a presence of the charges trapped at the interface; d) applying a readout bias potential sufficient to overcome a threshold of the liquid crystal layer; e) optically interrogating the liquid crystal layer to obtain an image having a spatial intensity correlated with a spatial dependence of the charges trapped at the interface; and f) directing the photoionization radiation into the liquid crystal layer and photoionizing the species within the liquid crystal layer, wherein a fluence of the photoionization radiation is selected to generate a sufficient concentration of mobile charge entities to reduce an effect of trapped charges located at or near an interface of the photoconductive layer.

In another aspect, there is provided a method of pre-conditioning an x-ray light valve imaging device, wherein the x-ray light valve imaging device includes a liquid crystal layer, a photoconductive layer, and electrodes for applying a potential bias across the liquid crystal layer and the photoconductive layer, wherein an electrode adjacent to the liquid crystal layer is optically transmissive; the method comprising the steps of: providing a photoionization radiation source for generating photoionization radiation having a wavelength suitable for photoionizing a species within the liquid crystal layer of the x-ray light valve imaging device; applying an initial bias potential between the electrodes for conditioning the photoconductive layer; and while applying the initial bias potential, directing the photoionization radiation into the liquid crystal layer and photoionizing the species within the liquid crystal layer, wherein a fluence of the photoionization radiation is selected to reduce an internal field within the liquid crystal layer.

In another aspect, there is provided a system for measuring x-ray images, said system comprising: an x-ray light valve imaging device including an electro-optic modulator layer, a photoconductive layer, and electrodes for applying a potential bias across said electro-optic modulator layer and said photoconductive layer, wherein an electrode adjacent to said electro-optic modulator layer is optically transmissive; a voltage source for applying a potential bias between said electrodes; an image readout device for optically interrogating said electro-optic modulator layer and obtaining an image having a spatial intensity correlated with a spatial dependence of trapped charges located at or near an interface of the photoconductive layer; a photoionization radiation source for providing photoionizing radiation, wherein photoionization radiation produced by said photoionizing radiation source has a wavelength selected to photoionize a species within said electro-optic modulator layer, and wherein a fluence of the photoionizing radiation is selected to generate a concentration of mobile charge entities for reducing an effect of the trapped charges; and a control and processing unit interfaced with at least the image readout device.

In another aspect, there is provided an x-ray light valve imaging device comprising: an electro-optic modulator layer; a photoconductive layer; and an intermediate layer provided between said electro-optic modulator layer and said photoconductive layer, said intermediate layer exhibiting spectrally selective optical transmission; and electrodes for applying a potential bias across said electro-optic modulator layer and said photoconductive layer, wherein an electrode adjacent to the electro-optic modulator layer is optically transmissive.

In another aspect, there is provided a method of erasing a residual image from a blocking-type photoconductive imaging device, the blocking-type photoconductive imaging device including a photoconductive layer, the method comprising the steps of: a) measuring the residual image; b) providing a photoexcitation radiation source for generating photoexcitation radiation with a wavelength suitable for photoexciting electron-hole pairs within the photoconductive layer; c) determining, based on the residual image, a prescribed spatial fluence profile for the photoexcitation radiation, such that when the photoexcitation radiation is directed into the photoconductive layer with the prescribed spatial fluence profile, a spatially-dependent concentration of electrons and holes are generated for locally reducing an effect of trapped charges located at or near an interface of the photoconductive layer; d) applying a reverse bias potential to the imaging device, the reverse bias potential having a polarity opposite to that of a previously applied exposure bias potential; and e) directing photoexcitation radiation with the prescribed spatial fluence profile into the photoconductive layer while applying the reverse bias potential, such that photoexcited electrons or holes drift towards and recombine with the trapped charges.

In another aspect, there is provided a system for measuring x-ray images, said system comprising: a blocking-type photoconductive imaging device, the blocking-type photoconductive imaging device including a photoconductive layer and electrodes for applying a potential bias across the photoconductive layer, wherein an interface of the photoconductive layer is suitable for trapping photoexcited charges under application of the potential bias; a voltage source for applying a potential bias between said electrodes; an image readout device for interrogating the imaging device and obtaining an image having a spatial intensity or signal correlated with a spatial dependence of charges trapped at the interface of the photoconductive layer; photoexcitation radiation source for generating photoexcitation radiation with a wavelength suitable for photoexciting electron-hole pairs within the photoconductive layer; and a control and processing unit interfaced with at least the image readout device.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
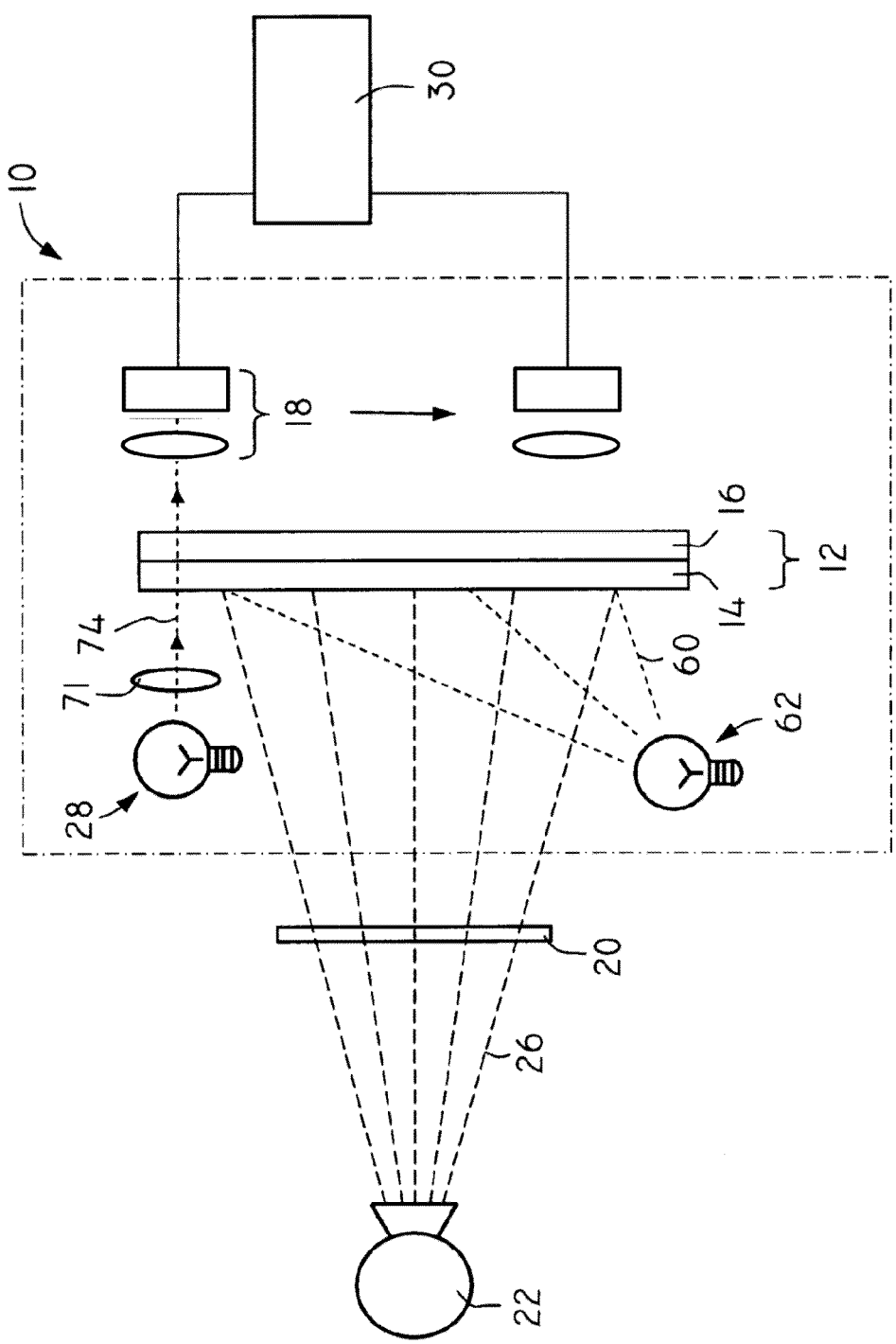
FIG. 1 illustrates an x-ray light valve (XLV) imaging system.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

As used herein, the term "resetting", when applied to a residual image in blocking-type photoconductive imaging device, means reducing the amount of trapped charges at an interface of the photoconductor layer, or reducing an effect of trapped charges at an interface of the photoconductor layer.

Embodiments of the present disclosure provide methods for the resetting of photoconductive imaging devices. In some embodiments, methods and devices are provided for the resetting of an x-ray light valve (XLV) imaging device, where photoionization radiation may be employed to actively reset an XLV device. Additional embodiments provide methods of optically resetting photoconductive imaging devices with spatially-dependent control, whereby the local flux of optical resetting radiation is determined according to a measured intensity of the image. While some embodiments provided herein relate to the resetting of XLV imaging devices it is to be understood that many of the embodiments disclosed herein may be employed for the resetting of a wide range of blocking-type photoconductive imaging devices, including, but not limited to, devices that are read using optical methods, electronic methods, or a combination thereof.

In a first embodiment, systems and methods are provided for resetting a blocking-type photoconductive imaging device according to a spatially varying fluence of photoexcitation radiation that is absorbed within the photoconductive layer. Without intending to limit the scope of the present embodiment, an example implementation is provided below involving the resetting of an XLV imaging device using spatially controlled photoexcitation radiation. Prior to describing the details of the present systems and method, a brief overview of XLV device is provided, and the need for resetting such devices is addressed.

XLV-based radiographic imaging systems include a photoconductive detector layer and an electro-optic light modulator (e.g. liquid crystal cell) layer. The photoconductive layer absorbs x-rays that have passed through an object to form a distribution of excited electrons and holes representing an exposure of the object. The x-rays absorbed by the photoconductive layer create a static electric field that can be optically interrogated and measured through the electro-optic light modulator, allowing the capture of the optical image to continue over a prolonged time. The stored optical image may be subsequently digitized by an optical scanning device.

FIG. 1 illustrates an example digital radiographic imaging system, which is shown generally at 10. The radiographic imaging system 10 allows x-rays that have passed through an object such as a patient to be captured and fed into a computer in a digital format.

The digital radiographic imaging system 10 combines an XLV 12, including a photoconductive detector layer 14 and an electro-optic light modulator 16, with a readout light source 28 and a digitizing optical scanning device 18. The XLV 12 is dimensioned so that the entire object or the desired area of interest of the object 20 can be imaged. The object 20 to be imaged is placed between the x-ray source 22 and the x-ray imaging system 10. The photoconductor layer 14 absorbs the x-rays 26 to create a static optical image in the electro-optic light modulator 16. By configuring the properties of the electro-optic light modulator 16 used, the image can remain stable on the order of minutes. The optical image stored in the electro-optic light modulator 16 is then digitized using the readout light source 28 and the optical scanning device 18, and processed through a processor 30. The system 10 may include focusing optics 71 for directing and focusing light from the readout light source 28 to the XLV 12.

Although the x-ray source 22 is shown on the photoconductor 14 side of the XLV 12 in FIG. 1, its position is not limited to the indicated side. The x-ray source 22 may be arranged on either side of the XLV 12 in different implementations since the x-rays 26 will typically not be significantly attenuated by the electro-optic light modulator 16 on their way to reach the photoconductor layer 14.

Figure 2:
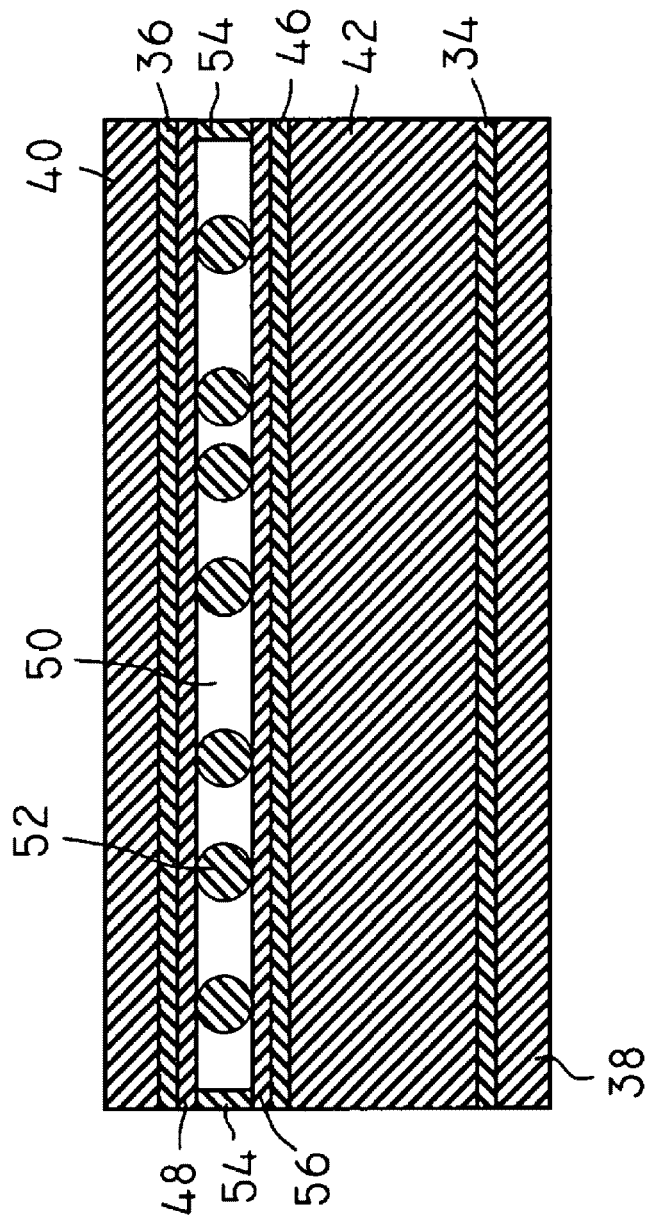
FIG. 2 is a cross-sectional view of an XLV, forming part of the shown in FIG. 1.

Turning now to FIG. 2, the example XLV 12 is illustrated in additional detail. In this example, amorphous selenium is employed as the photoconductor 14 and a liquid crystal cell is provided as the electro-optic modulator 16, and transparent electrodes, 34 and 36, are included on either side.

An example XLV imaging device may be constructed as follows. Two transparent substrates, 38 and 40, with deposited electrodes, 34 and 36, may be provided. The substrate may be formed from glass plates, with indium tin oxide (ITO) electrodes, 34 and 36. The layer of amorphous selenium 42 is deposited onto one of them. When used in reflective configuration, the substrate on the photoconductor side 38 does not need to be transparent and a metal plate can be used instead, such as aluminum, with the plate acting as an electrode and the metal oxide acting as a blocking layer. Using glass for both substrates 38 and 40 has the advantage that visible light can be provided from the side of the photoconductor 14.

The layer of amorphous selenium 42 is deposited across the area of the substrate 38, with a thickness set to achieve a desired level of x-ray absorption efficiency, usually in a range from about 50 to about 1000 µm. If desired, one or more additional layers 46 is deposited onto the amorphous selenium 42 layer. Very thin alignment layers, 48 and 56, are then applied on both surfaces. They are then cured and formed by using light, mechanical rubbing, or other means.

Both substrates 38 and 40, with all the additional layers 42, 46, 56, and 48, are subsequently made into a sandwich structure that will contain the liquid crystal 50. The transparent substrate 40 with the alignment layer 48 is placed in a spacer distributor and sprayed with spacers 52. The purpose of the spacers 52 is to keep a constant gap, which will later be filled with the liquid crystal 50. Adhesive 54 is placed around the perimeter of the transparent substrate 40 with the alignment layer 48, allowing an opening (neck) for the liquid crystal 50 to be added later. The two substrates, 38 and 40, with all the additional layers 42, 46, 56, and 48 in place, are then sandwiched together and placed in a press to ensure that the correct cell gap is maintained while the adhesive 54 cures. The cured structure is put in a vacuum chamber, which is evacuated. The liquid crystal 50 is then added at the location of the neck in the adhesive gasket using a vacuum manipulator and allowed to fill the cell by capillary action. Once the cell is filled, it is pressed again to ensure a correct gap, and sealed (while under pressure), producing the finished XLV 12.

The choice of liquid crystal 50 used in the cell varies the properties of the resulting electro-optic light modulator 16. For example, by using high-resistivity liquid crystals designed for active-matrix liquid-crystal displays, the capability of keeping charge can be greatly increased. Such high-resistivity liquid crystals are designed for applications where charges need to be stored in the pixel of a liquid-crystal display until the pixel is addressed in the next driving frame. The capability of keeping charge is called Voltage Holding Ratio (VHR). It usually depends on the chemical structure of the liquid crystal, the alignment layer, the handling of the liquid-crystal cell, and other factors (water content, impurities, glass, etc.). Increased concentration of organic or inorganic impurities will reduce the VHR. Large VHR can only be achieved with high resistivity liquid-crystal mixtures and extra pure materials.

To minimize organic contaminations, rigorous cleaning of the substrates and alignment layers based on linear photo-polymerization is important. By using ultra-pure materials, alignment layers 48 and 56 based on linear photo-polymerization, and a high-resistivity liquid crystal 50 in combination with rigorous cleaning procedures, proper handling, and avoiding contaminations, the electro-optic light modulator 16 can be configured to retain the optical image for a long period of time, typically on the order of minutes.

In some example implementations, the liquid crystal may be selected from a group of nematic liquid crystals which are sensitive for electro-optical modulation. Example nematic liquid crystals include, but are not limited to, E7 available from EMD Chemicals), and ZL1-4792 (available from Merck and Co., Inc.). In another example, the liquid crystal may be a polymer dispersed liquid crystal. The liquid-crystal cell used as the electro-optic light modulator 16 may be designed to accommodate specific wavelength(s), viewing and electro-optical properties. However, the greatest variations may arise from using different liquid-crystal-cell designs. Suitable implementations include transmissive and reflective twisted nematic cells with various twist angles, including a zero twist angle.

Although the preceding construction method described the liquid-crystal cell used as the electro-optic light modulator 16 as having the same alignment on both sides, other implementations may include alignment layers, 48 and 56, made from the same or different materials, which may have different properties, such that pre-tilt and alignment can vary from side to side of the liquid-crystal cell.

Figure 3:
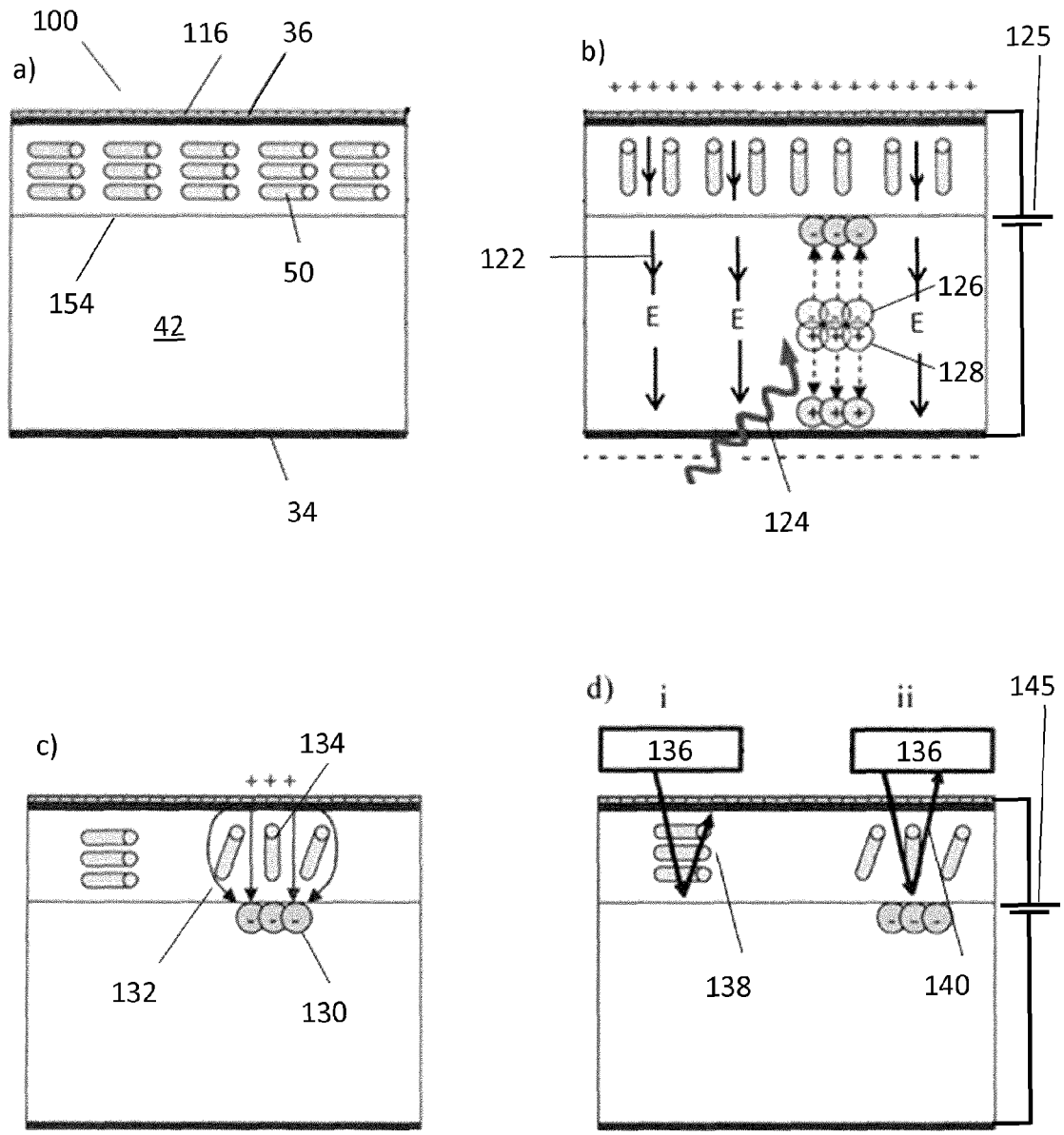
FIGS. 3(a)-(d) illustrate the formation of an image in an XLV device and the subsequent readout of the image using an external optical source.

The general operation of an XLV device is now illustrated in FIGS. 3(*a*) to 3(*d*). Referring to FIG. 3(*a*), an XLV is shown generally at 100. The XLV 100 allows x-rays that have passed through an object (such as a patient) to be captured and provided to a control and processing system (described further below) in a digital format. As described previously, XLV 100 includes photoconductor layer 42, a liquid crystal cell 50, a top electrode 36, and a bottom electrode 34. In FIG. 3, additional layers that were shown in FIG. 2 such alignment layers, 48 and 56, substrates 38 and 40, and additional layer 46, are not shown for simplicity, although it is to be understood that these layers may be present. Polarizing filter 116 may be included as a layer of device 100, or provided externally.

As noted above, the photoconductor may be amorphous selenium (a-Se). Other suitable photoconductors include silicon, amorphous selenium, stabilized amorphous selenium, hydrogenated amorphous silicon (a-Si:H), cadmium zinc telluride (CZT), lead oxide (PbO), lead iodide (PbI2), gallium arsenide, mercury iodide (HgI2) and chalcogenide glass. Advantages of using a-Se include high absorption coefficient, large quantum efficiency, ease in depositing as compared to the crystalline semiconductor, bipolar charge transport, non-dispersive transport, and relatively small dark current compared to other photoconductors.

FIGS. 3(*b*)-(*d*) illustrate the steps in measuring an image with an XLV imaging device. Referring to FIG. 3(*b*), an exposure bias potential 125 is applied between electrodes 34 and 36 to generate electric field 122. Electrode 36 is optically transmissive to allow the propagation of an external light beam into the liquid crystal layer 50. As an example, electrode 36 may be at high electric potential and electrode 34 may be at low electric potential, though the opposite polarity may be employed. The magnitude of the exposure bias potential 125 depends on the thickness of the XLV 100. The electric field required in the photoconductor layer 42 is usually in a range of about 5 to about 100 V per micron. For example, if the thickness of the photoconductor layer is 1000 microns and the thickness of the electro-optic light modulator is 5 microns, an exposure bias potential of 10,050 V will be applied to the electrodes 34 and 36 to achieve an electric field of 10 V per micron in the photoconductor 42.

When photoconductive layer 42 absorbs an x-ray 124 during imaging, an electron-hole pair is produced inside the photoconductive detector layer 42. As an illustration, electron-hole pairs are shown as electrons 126 and holes 128. Exposure bias potential 125 causes electrons 126 to drift towards electrode 36, and holes 128 to drift towards electrode 34. Electrons 126 are trapped at trap states residing at the interface 154 of photoconductive layer 42 and liquid crystal layer 50. The resulting charge image collected at the photoconductor-modulator interface 154 faithfully reproduces the absorbed x-ray intensity pattern, causing spatial variations in the electric field across the electro-optic light modulator.

After charges 126 are trapped at or near the interface, the residual trapped charges create a local electric field that is related to the intensity of the absorbed x-rays. This residual field alters the orientation of the liquid crystal director, as shown in FIG. 3(*c*) where the trapped electrons 130 produce local residual field 132 that locally rotates liquid crystal molecules 134.

The strength of the local residual field may be interrogated by passing an optical beam through the liquid crystal layer 50 and measuring the optical power after the beam is reflected by the interface of the liquid crystal layer 50 and the photoconductive layer 42. An example method of optical interrogation is shown in FIG. 3(*d*) where scanner 136 moves from location i to location ii corresponding to regions without and with a residual field, respectively. At location i, the lack of a residual field causes the polarization rotation and subsequent extinction of the incident beam 138. However, at location ii, the presence of the local field and the resulting rotation of the liquid crystal director field changes the amount of polarization rotation of the incident beam 140 and results in the detection of signal by the scanner 136.

The scanner 136 may, in selected non-limiting embodiments, include a low-divergence light source such as a laser, or any other light source that illuminates the liquid crystal cell 50. Alternatively, separate illumination and detection apparatus may be employed to optically interrogate the liquid crystal layer. The scanner 136 may include a light detector such as a single photo-detector, or it may include an array of photo-detectors (e.g. a camera). Those skilled in the art would appreciate that there are many methods to detect the variations in electric field in the liquid crystal layer 50 and that the methods disclosed herein are merely provided as examples. It is to be understood that scanner need not optically interrogate different spatial regions of an XLV imaging device one at a time, but may interrogate multiple spatial regions in parallel.

It is common for electro-optic light modulators, such as liquid crystals, to have a threshold voltage, which has to be reached before they can respond optically. As a consequence, some parts of the charge image created at the photoconductor-modulator interface 154 may not be represented in the static optical image. In order to avoid this situation, there are several methods of biasing the XLV 100 during digitization of the optical image after a given x-ray exposure. These techniques aim to bring the electro-optic light modulator 16, particularly in case of a liquid-crystal cell 50, to the threshold of its operating characteristic, to enhance the signal, reduce the noise, or shift the optical response as a function of exposure.

In one embodiment, the XLV 100 can be biased using radiation. This can be done by using light source 62 (shown in FIG. 1), performing a flood field exposure with light 60 to which the photoconductor is sensitive and creating additional uniformly distributed charge in the photoconductor 14. Although in FIG. 1 light source 62 is indicated to be on the photoconductor 14 side of the XLV 12, in different embodiments it might be positioned to illuminate the photoconductor 14 through the electro-optic light modulator 16. Radiation-based biasing can be performed before or after x-ray exposure. It can also be done during the digitization phase by using light source 28 with the readout light 74 tuned to a wavelength to which the photoconductor is sensitive.

Alternatively, XLV 100 can be biased directly by applying a readout bias potential, shown in FIG. 3(*d*) at 145, to the electrodes 34 and 36 during digitization of the optical image. The electric field required in the electro-optic light modulator 16 is usually in a range of about 0 to about 4 V per micron. For example, if the threshold voltage of the electro-optic light modulator is 1 V, the thickness of the photoconductor layer 14 is 1000 microns, and the thickness of the electro-optic light modulator 16 is 5 microns, one can apply to the electrodes 34 and 36 a readout bias potential of 201 V to overcome the threshold voltage on the assumption that the dielectric constants of the photoconductor and the electro-optic light modulator are the same. Higher readout bias potentials are used to increase the signal, while lower bias potentials are used to reduce the effect of offset signal. It has been found that using a readout bias potential is a much more flexible and convenient way to shift the response characteristics of the electro-optic light modulator. It allows multiple shifts to be done on a single x-ray exposure, which is not convenient when the biasing is done with actinic light. Although read-out bias potential 145 is shown as only being applied during optical interrogation of the liquid crystal in FIG. 3(*d*), the bias potential need not be removed between application of exposure bias potential 125 and read-out bias potential 145, and exposure bias potential 125 may be directly reduced to the appropriate read-out bias potential prior to optical interrogation.

After scanning the stored image in XLV 10, it is desirable to erase or reduce the residual electric field 132 produced by the trapped charges. As noted above, such residual fields produce ghost images that reduce the signal-to-noise ratio and sensitivity of the imaging device.

Figure 4:
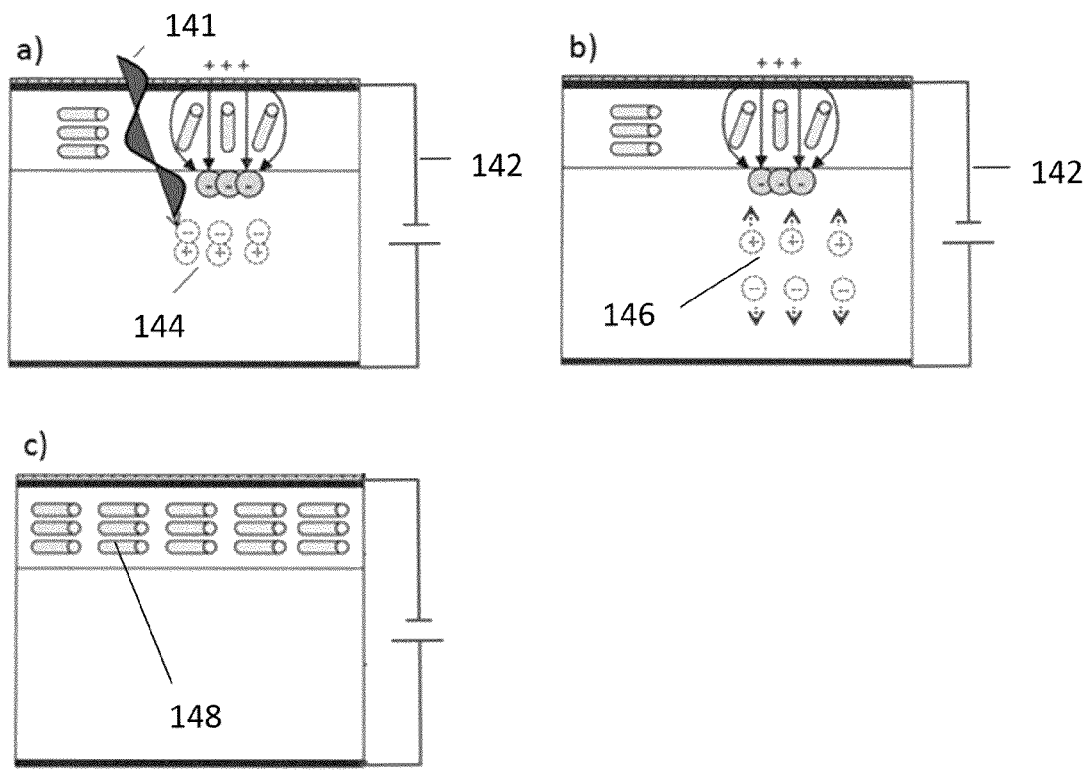
FIGS. 4(a)-(c) illustrate the steps of measuring an image from an XLV imaging system and subsequently illuminating the XLV with photoexcitation radiation having a spatial intensity profile corresponding to the measured image.

In one embodiment, shown in FIG. 4(*a*), the device is irradiated with photoexcitation radiation 141 under the application of a reverse bias voltage 142, where the photoexcitation radiation photoexcites carriers in the photoconductive layer 42. In contrast with known image erasure methods, photoexcitation radiation 141 does not simply flood photoconductive layer 42 of the imaging detector. Instead, photoexcitation radiation 141 irradiates the imaging device with a spatial profile that is related to the image acquired during the previous readout step (after exposure). This delivers a controlled and spatially tailored fluence of photoexcitation radiation to the photoconductive layer, thereby generating spatially-dependent local concentrations of charge pairs that provide improved neutralization of the trapped charge.

The fluence of the photoexcitation radiation received at a given pixel or spatial location in the imaging detector may be related to the intensity of the image at the given pixel in a monotonic relationship, such that a given local image intensity is associated with a single local fluence of photoexcitation radiation. The relationship may involve a linear dependence of fluence on local image intensity or signal strength. For example, the prescribed fluence of the photoexcitation radiation received at a given pixel or location in the imaging detector may be proportional to the intensity or signal at the corresponding location in the image. The relationship may include a linear range.

The wavelength of the photoexcitation radiation is selected to generate charge pairs 144 in the photoconductive layer 42, and the wavelength may be chosen such that charge pairs are generated near the interface 154 where the trapped charges reside. This may be achieved by irradiating the device from the side closest to the interface 154, as illustrated in FIG. 4(*a*).

The wavelength of the photoexcitation radiation may be selected so that the absorption depth of the photoexcitation radiation in the photoconductive layer is shallow compared to the total thickness of the photoconductive layer (i.e. such that a substantial portion of the photoexcitation radiation is absorbed adjacent to the interface where the charges are trapped). In the case of a photoconductive layer made from amorphous selenium, the wavelength of the photoexcitation radiation may be chosen to lie with a range of approximately 350 to 700 nm. The application of the reverse bias voltage 142 causes carriers 146 having a polarity opposite to that of the trapped charges to drift toward and recombine with the trapped charges, as shown in FIG. 4(*b*), thereby substantially reducing the residual field and producing a substantially unperturbed director 148 as shown in FIG. 4(*c*). The reverse bias voltage generally depends on this thickness of the photoconductive layer, and may be within the range of approximately 10 to 10,000 volts. In one example, the magnitude of the reverse bias voltage is approximately less than or equal to the magnitude of the forward bias voltage that is applied during exposure.

While the present disclosure describes photoexcitation radiation in terms of its fluence, it is to be understood that other related properties may also be controlled, such as, but not limited to, intensity, power, energy flux, irradiation time, and any combination thereof.

Figure 5:
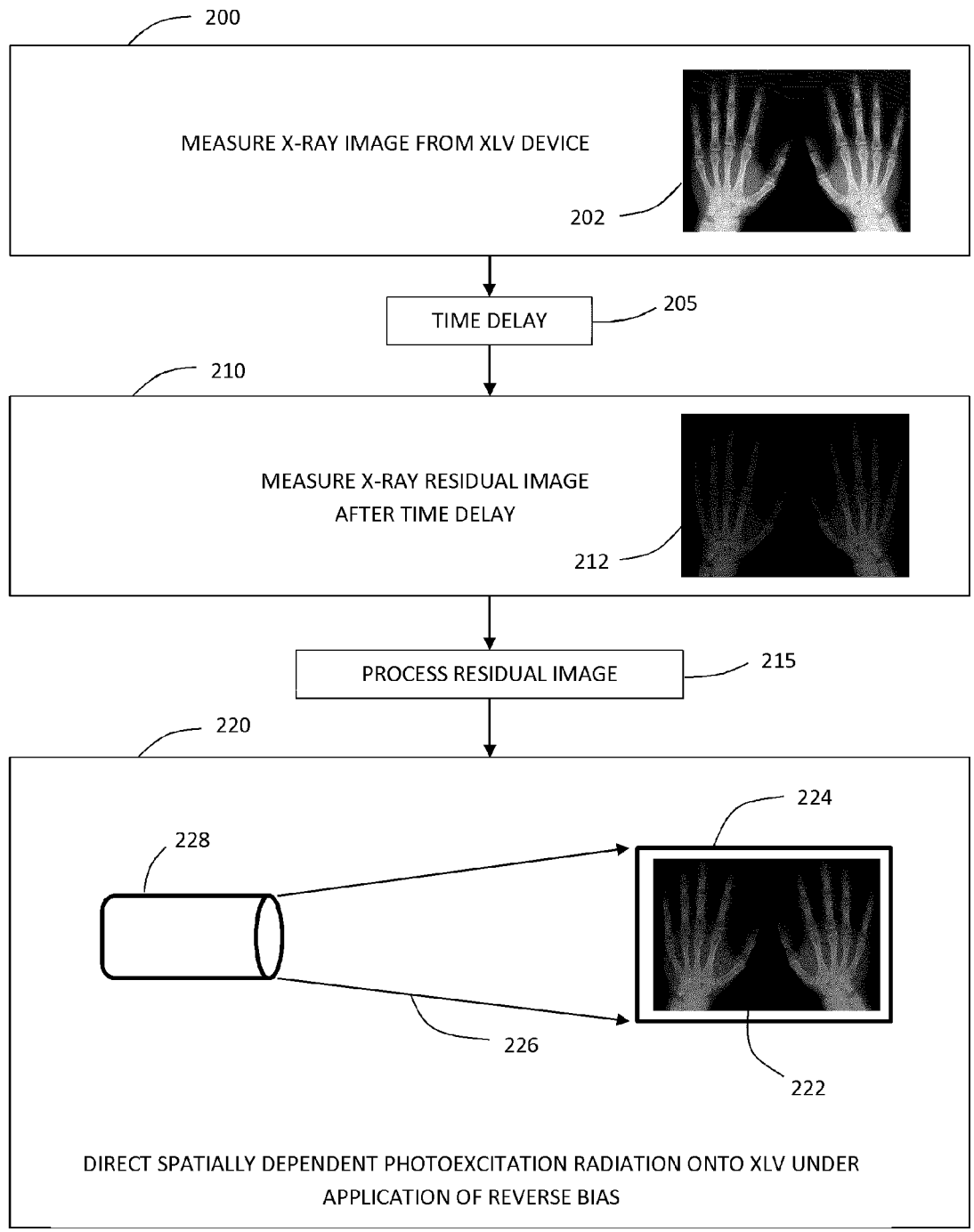
FIG. 5 illustrates a method of erasing an image in a photoconductive imaging device using spatially controlled photoexcitation radiation.

FIG. 5 illustrates the application of the present embodiment for the resetting of a blocking-type photoconductive imaging detector. In step 200, the imaging device is employed to obtain an x-ray image 202 of an object. In the present example, an x-ray image of two hands is shown. Having obtained the image, the trapped charges will slowly dissipate through time, such that residual charges remain and decay with time. After some time delay 205, but prior to measuring a subsequent image using imaging radiation, it is therefore important to perform an erasing step.

In the Figure, the erasing of the photoconductive device is shown in steps 210, 215 and 220. In step 210, a residual image is measured without further application of any imaging x-rays. The residual image 212 is shown as a fainter version of the original image. This residual image is processed in step 215 and a suitable spatial fluence profile is determined for the subsequent irradiation step involving the photoexcitation radiation. As noted above, this step may be performed by processing the recorded residual image and employing calibration data to determine the appropriate fluence. Finally, in step 220, the imaging device 224 is irradiated by photoexcitation radiation 226 produced by source 228. As shown in the Figure, the photoexcitation radiation 226 is directed onto device 224 with a spatially dependent fluence 222 that is selected to erase, or at least partially erase, the residual image.

While the above embodiment relates to a method in which a positive image is measured by the photoconductive detector, other embodiments may utilize a different configuration of the apparatus in which a negative image is measured. In such a case, the spatial fluence profile of the photoexcitation radiation is based on the negative of the measured image (i.e. an inverse correlation), so that a higher fluence of photoexcitation radiation at a given pixel corresponds to a higher concentration of locally trapped charges.

Figure 6:
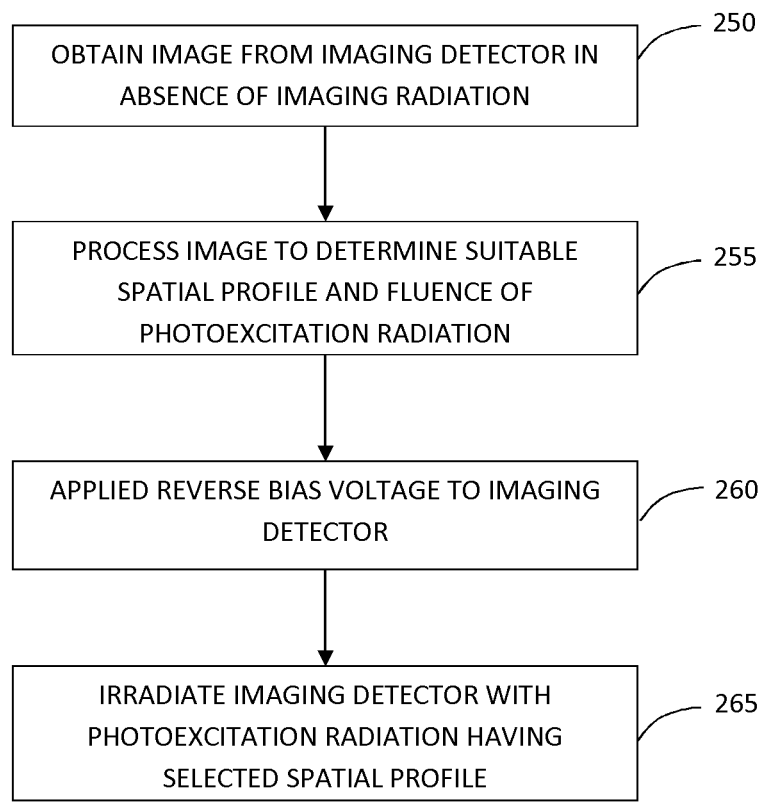
FIG. 6 is a flow chart illustrating a method of employing photoexcitation radiation for use in a resetting operation.

FIG. 6 provides a flowchart that illustrates the aforementioned method of resetting a blocking-type photoconductive imaging device. In step 250, the photoconductive imaging device is measured in the absence of imaging radiation in order to determine the spatial profile and intensity of the residual charges, thereby obtaining the residual image. As noted above, the residual image is obtained prior to performing an imaging measurement. For example, the residual image may be obtained immediately prior to performing an imaging measurement, in order to obtain a recent characterization of the residual charges trapped at the interface within the device. The residual image may also be a recently acquired image obtained after having applied imaging radiation onto the device.

According to step 255, the residual image is processed to determine a suitable spatial profile and fluence of the photoexcitation radiation, where the fluence and spatial profile are selected to provide at least partial neutralization of trapped charges. As described below, the appropriate spatial profile and fluence may be determined according to previously measured calibration data.

In step 260, a reverse bias field is applied to the imaging detector to achieve charge separation and drift upon irradiation with the photoexcitation radiation. The bias is applied in a reverse polarity to the bias applied during the initial imaging step. Finally, in step 265, the imaging detector is irradiated with the photoexcitation radiation according to the spatial profile and fluence determined in step 255. The reverse bias may be removed after performing the irradiation step.

Figure 7:
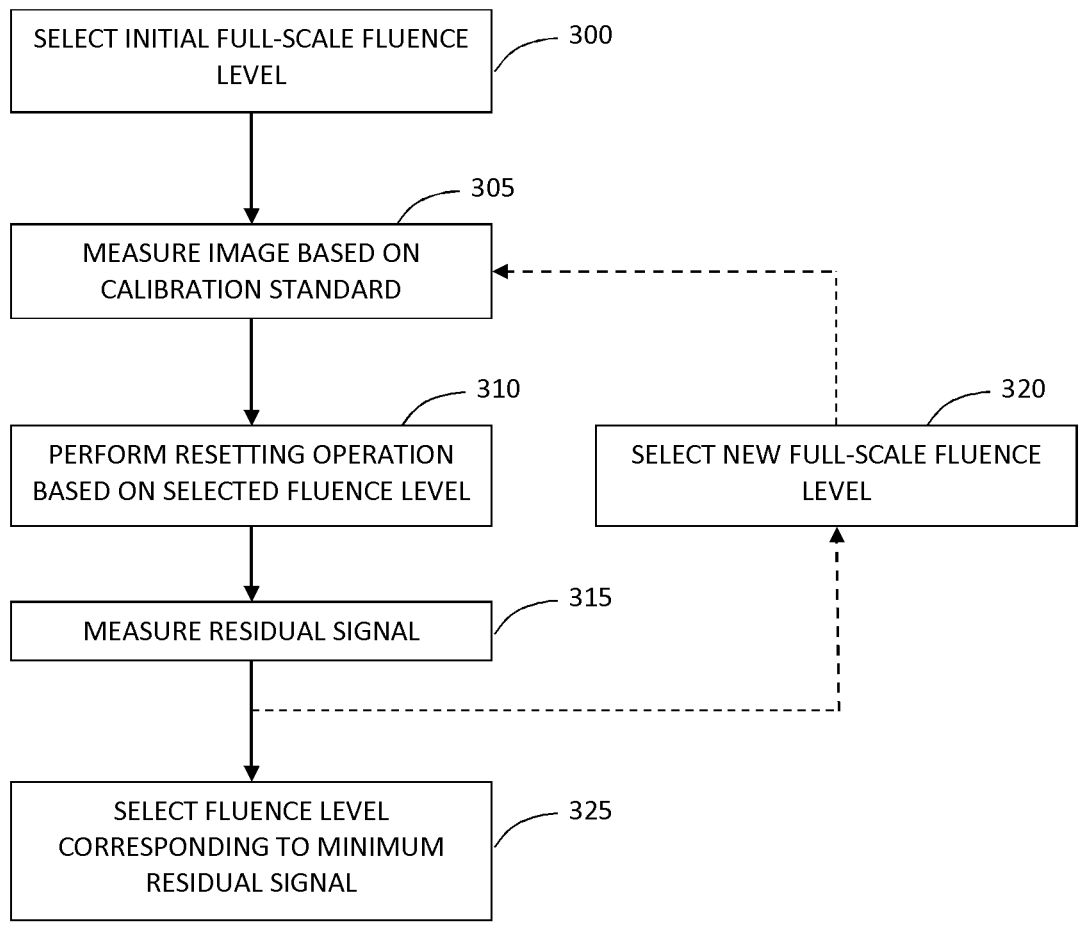
FIG. 7 is a flow chart illustrating a method of calibrating the fluence of photoexcitation radiation for use in a resetting operation.

The intensity of the generated image may be adjusted to produce a desired level of resetting (i.e. local charge neutralization). In one embodiment, as shown in the flow chart provided in FIG. 7, a desired fluence of the photoexcitation radiation may be determined in a calibration process. In one non-limiting embodiment, a reference subject having a selected image spatial profile is employed to generate a calibration image, and multiple image acquisitions and resetting operations are performed in order to determine optimal fluence of photoexcitation radiation.

In step 300, an initial full-scale fluence level (i.e. a level corresponding to a maximum image intensity level) is initially selected. An image of the reference standard is then measured in step 305. In step 310, the resetting method outlined above is employed to reset the detector, where the spatial profile of the photoexcitation radiation is selected based on the spatial profile of the measured image. Finally, in step 315, the residual image signal is measured to determine the degree of resetting. These steps are repeated one or more times, varying the full-scale fluence level for each measurement at step 320. Finally, in step 325, a full-scale fluence level corresponding to a desired degree of resetting is selected. In one example embodiment, the full-scale fluence level that corresponds to the minimum residual signal is selected. The above calibration method may be repeated with one or more additional standards to confirm or refine the selected fluence parameters.

In one embodiment, the reference subject produces images with a wide dynamic range and with repeatable spatial features, thus enabling the calculation of statistical measures such as noise parameters for use determining a signal to noise ratio, limit of detection, and/or dynamic range, and resolution.

Figure 8:
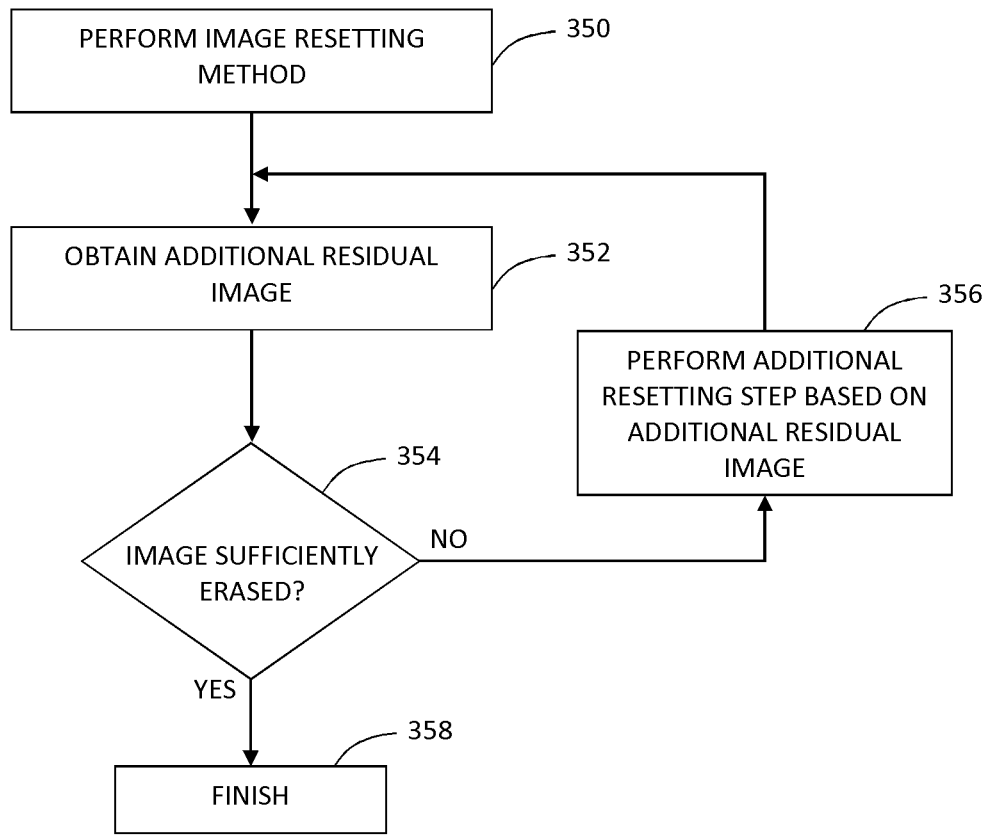
FIG. 8 is a flow chart illustrating an iterative method of resetting a photoconductive imaging device using photoexcitation radiation that is spatially correlated with an initial residual image.

Having performed the above method of resetting the imaging detector, a small amount of trapped charge may remain. A method of reducing this trapped charge is provided in FIG. 8. To infer the success of the resetting process, an additional residual image is measured in step 352 (again, in the absence of imaging radiation) after having previously performed a resetting operation in step 350. The additional residual image obtained in this manner will be due to the residual trapped charge. If it is determined that an insufficient degree of resetting has been performed in step 354, then this additional image may be used as the basis for a further resetting step (step 356), performed according to the above embodiment. This procedure may continue iteratively, and stopped at step 358 after a sufficient degree of resetting has been accomplished. In other words, by iterating as many times as required, the resetting operation can reduce the amount of remaining charge buildup to a level below a desired threshold.

Figure 9:
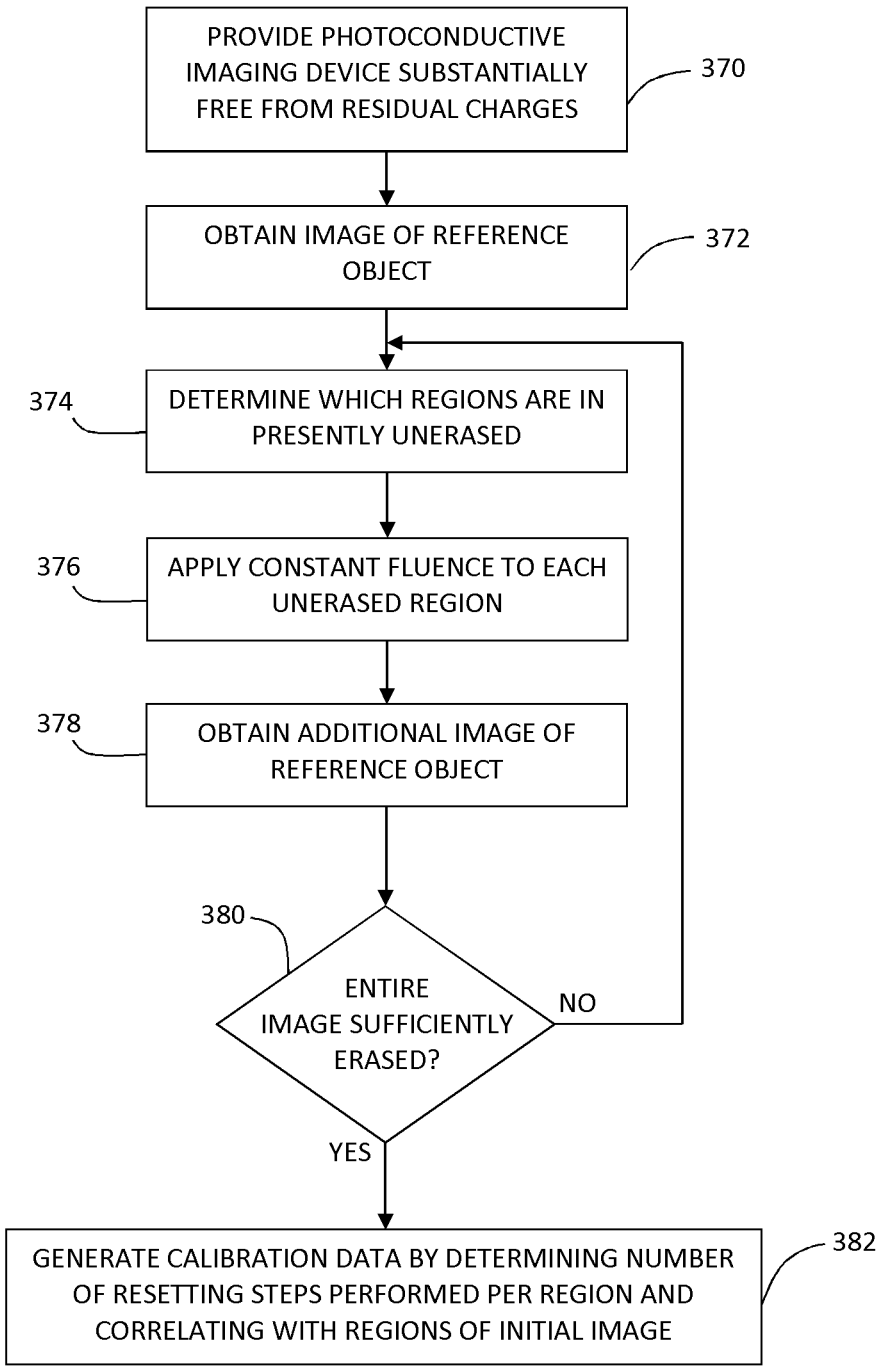
FIG. 9 is a flow chart illustrating a method of determining a calibration relation between the residual image intensity and the photoexcitation radiation.

In another embodiment, the calibration of the photoexcitation radiation fluence may be performed through a serial process, involving the spatially-dependent application of multiple exposures at a given fluence of the photoexcitation radiation until satisfactory erasure is achieved. FIG. 9 illustrates an example implementation in which the method may be performed as follows. In step 370, a blocking-type photoconductive imaging device is initially provided that is substantially free from residual charges. A reference image is then obtained of a reference object in step 372, in which imaging radiation is directed through the object and onto the photoconductive imaging device and an image is subsequently obtained.

In one embodiment, the reference object is prepared for imaging such that the object is capable, when imaged onto the device by the x-ray, and owing to its shape and thickness variation, of generating an image with spatial variations spanning a diverse range of possible image signal or intensity values. In one example, the range of value is selected to span the range of values that is anticipated to occur in normal operation.

Having obtained the reference image, a determination is made of which spatial regions of the imaging device are in need of erasure in step 374. For example, regions (or pixels) that require erasure may be those regions for which the image signal or intensity exceeds a selected threshold or minimum value. In step 376, photoionizing radiation is directed on the device such that the regions requiring erasure each receive a substantially equivalent fluence.

The level of the equivalent fluence applied to the unerased regions in step 376 is selected to be a fraction of the maximum achievable fluence, or a fraction of the fluence required to erase the portion of the reference image with a maximum exposure. For example, the achievable fluence may be represented by a number of different levels or discrete unit dosages, for example, F=0 to F=N, such that F=0 represents the absence of photoexcitation radiation, while F=N represents the maximum fluence. These steps may relate to the actual fluence in such a way that F=N will satisfactorily erase the maximum expected pixel intensity, based on prior experimental determination. The level of equivalent fluence applied to each unerased portion may be selected to correspond to F=1.

After having applied the photoexcitation radiation a first time, a determination is made in step 380 as to whether or not the entire image has been erased. Since only one application of the photoexcitation radiation has been provided at this point in the method steps, it is likely that a significant portion of the residual image will require further erasing. Accordingly, steps 374 to 378 are repeated, such that a determination is made as to which regions of the device remain unerased, and a constant level of photoexcitation radiation is applied to each unerased region.

This process is repeated until it is determined in step 380 that the entire image has been sufficiently erased. A calibration relation may then be determined based on correlating the number of erasure steps applied to a given region with the initial image intensity in that region, where this step is performed for all regions on the device. The resulting calibration data correlating the net fluence required for erasure with the initial image intensity may then be employed to construct a calibration relation. This may be achieved, for example, by mathematically fitting the measured calibration data to a mathematical relation, or for example, by generating a lookup table.

It is to be understood that the choice of the level of the constant fluence applied (or equivalently, the value of N in the above example), determines the number of data points in the calibration relation. As such, it may be desirable to choose a sufficiently large value of N, or equivalently, a sufficiently small value for the constant applied fluence, such that a sufficient number of data points are obtained. It should be appreciated, however, that obtaining a large number of data points may lead to a calibration that is not accurate due to decay of the residual image during the measurement process. Accordingly, one may choose a number of data points such that the effect of the inherent decay of the residual image is sufficiently small to avoid errors in the calibration process.

It should be noted that the initial image may contain many common pixels with the same intensity. In such a case, the total applied fluence for pixel of the common pixels may be slightly different. This difference may arise, for example, due to system imperfections, such as noise, nonlinearities, and local material variations. For example, a criterion such as average or peak value may be used to determine an appropriate value from the various fluence values measured. It should also be recognized that the effect of the stepwise (i.e. serial) application of photoexcitation radiation may not be identical to that the effect of an equivalent fluence when delivered all at once (i.e. as a "single shot"). As a consequence, the calibration data, as determined above, may benefit from a subsequent correction step, such as the application of a scaling factor. An appropriate correction may be determined by routine experimentation.

Figure 10:
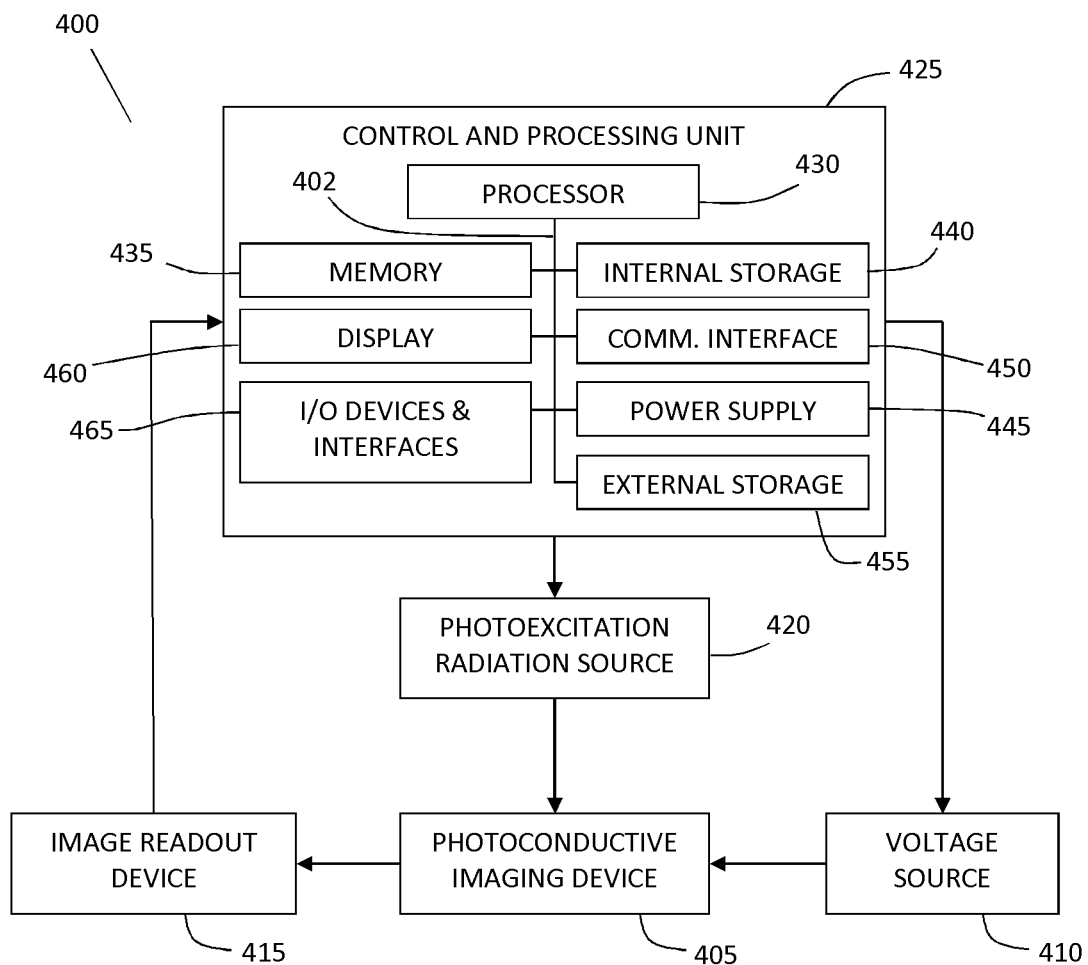
FIG. 10 provides a block diagram of an XLV imaging system suitable for erasure with spatially-controlled photoexcitation radiation.

Referring now to FIG. 10, an illustration is provided of a system 400 for performing an imaging measurement using a blocking-type photoconductive imaging detector, and resetting the imaging detector using photoexcitation radiation having a spatial profile related to a previously measured image. System 400 includes a photoconductive imaging device 405, voltage source 410 (for applying a forward bias across imaging detector 405 while performing an imaging step, and a reverse bias during a resetting operation as described above), image readout device 415, photoconductive radiation source 420, and control and processing unit 425, the latter of which is described in further detail below.

The image is obtained using image readout device 415, which may detect the imaging signal using an optical (e.g. as described above for XLV devices) or an electrical read out modality (e.g. direct readout of current from a pixelated imaging device), or a combination thereof. In one embodiment, an electrical-based image acquisition subsystem may be integrated with photoconductive imaging device 405 to form a composite imaging and readout apparatus.

Control and processing unit 425 is interfaced with image readout device 415 and the photoexcitation radiation source 420. Control and processing subsystem 425 receives image data from image readout device 415 and provides to photoexcitation radiation source 420 a determination of an appropriate spatial profile and fluence of photoexcitation radiation for efficient and spatially tailored neutralization of trapped charge. Photoexcitation radiation source 420 includes all necessary optical components for the delivery of the appropriate spatial profile of the photoexcitation radiation to the imaging detector. Optical components may include, but are not limited to, imaging components such as lenses, mirrors, and optical scanning subsystems.

The photoexcitation radiation may be provided with a system that illuminates the imaging detector in a serial (i.e. scanned) or parallel format, provided that the source has a wavelength selected to enable the excitation of carriers at a desired depth within the photoconductive layer, and with a sufficient power to generate a concentration of charge carriers for at least partially neutralizing the trapped charges. Suitable sources include, but are not limited to, lasers, one or more light emitting diodes, incandescent light sources, and fluorescent lamps. In one embodiment, a single source is modulated, scanned and focused onto the imaging detector. In another embodiment, an array of sources delivers spatially modulated irradiation that is imaged onto or butt coupled to the imaging detector. In an embodiment in which the imaging detector is optically interrogated to measure an image (such as an XLV), the readout and resetting radiation may be provided by a common broadband or multi-wavelength source that is spectrally controlled (e.g. selectively filtered) to deliver either the readout radiation or photoexcitation radiation as required.

Some aspects of the present disclosure can be embodied, at least in part, in software. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's).

FIG. 10 provides an example implementation of control and processing unit 425, which includes one or more processors 430 (for example, a CPU/microprocessor), bus 402, memory 435, which may include random access memory (RAM) and/or read only memory (ROM), one or more internal storage devices 440 (e.g. a hard disk drive, compact disk drive or internal flash memory), a power supply 445, one more communications interfaces 450, external storage 455, a display 460 and various input/output devices and/or interfaces 455 (e.g., a receiver, a transmitter, a speaker, a display, an imaging sensor, such as those used in a digital still camera or digital video camera, a clock, an output port, a user input device, such as a keyboard, a keypad, a mouse, a position tracked stylus, a position tracked probe, a foot switch, and/or a microphone for capturing speech commands).

Although only one of each component is illustrated in FIG. 10, any number of each component can be included control and processing unit 400. For example, a computer typically contains a number of different data storage media. Furthermore, although bus 402 is depicted as a single connection between all of the components, it will be appreciated that the bus 402 may represent one or more circuits, devices or communication channels which link two or more of the components. For example, in personal computers, bus 402 often includes or is a motherboard.

In one embodiment, control and processing unit 425 may be, or include, a general purpose computer or any other hardware equivalents. Control and processing unit 425 may also be implemented as one or more physical devices that are coupled to processor 430 through one of more communications channels or interfaces. For example, control and processing unit 425 can be implemented using application specific integrated circuits (ASIC). Alternatively, control and processing unit 425 can be implemented as a combination of hardware and software, where the software is loaded into the processor from the memory or over a network connection.

Control and processing unit 425 may be programmed with a set of instructions which when executed in the processor causes the system to perform one or more methods described in the disclosure. Control and processing unit 425 may include many more or less components than those shown.

While some embodiments have been described in the context of fully functioning computers and computer systems, those skilled in the art will appreciate that various embodiments are capable of being distributed as a program product in a variety of forms and are capable of being applied regardless of the particular type of machine or computer readable media used to actually effect the distribution.

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like.

Figure 11:
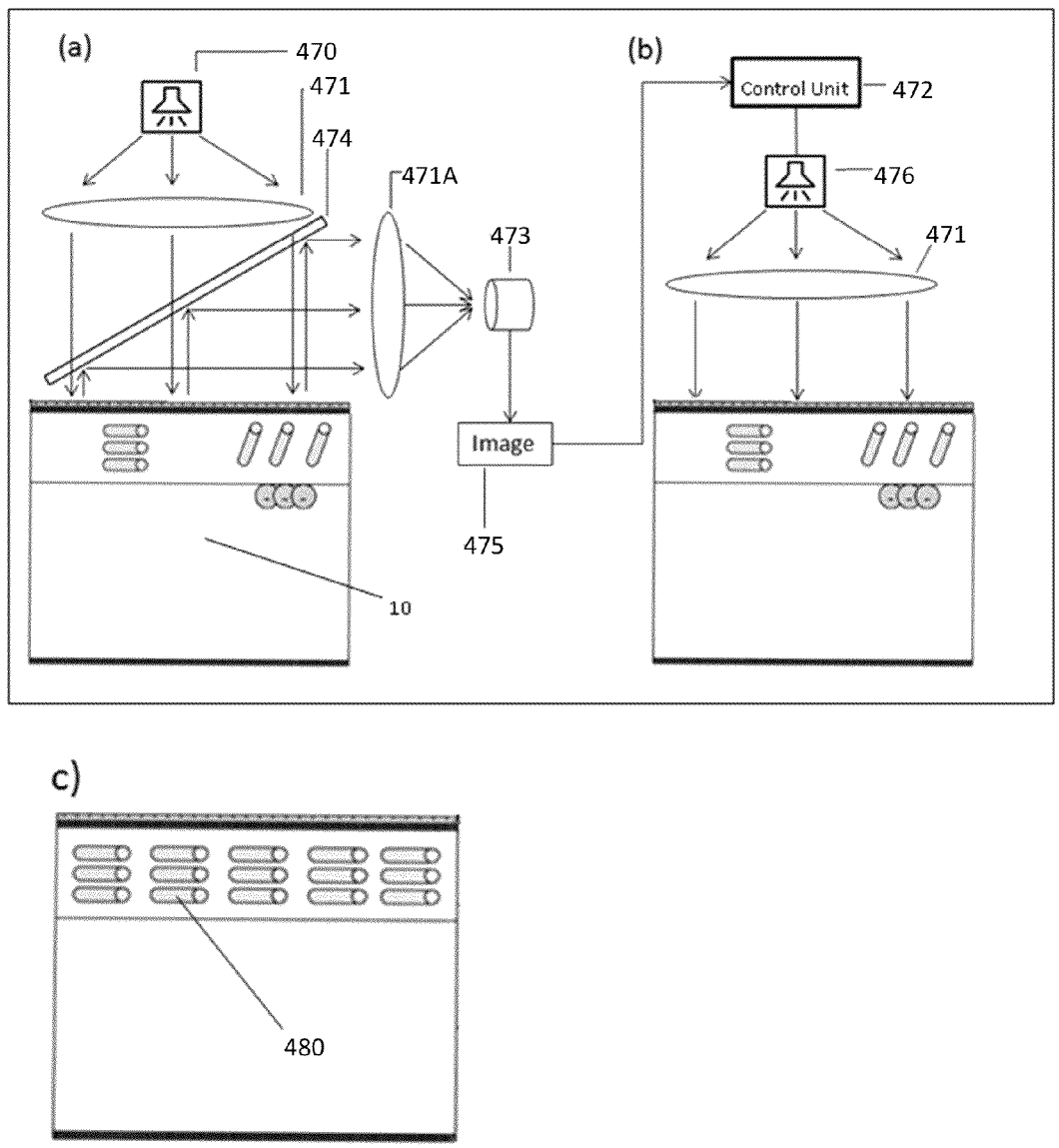
FIGS. 11(a)-(c) illustrate the steps of measuring an image from an XLV imaging system and subsequently illuminating the XLV with photoexcitation radiation having a spatial profile corresponding to the measured image.

An example implementation of a read-out and resetting apparatus is shown in FIG. 11, in which the image is read out by a camera. Light from source 470 is collimated by focusing element 471 and reflected or scattered off the XLV 10 and focused through second focusing element 471A onto camera 473. Half-silvered mirror or beamsplitter 474 allows camera 473 to pick-up and store the image 475. During a resetting operation, light source 470 is replaced by photoexcitation radiation projector 476, which projects photoexcitation radiation onto the XLV via focusing element 471. The stored image is used to program a projector through control unit 472, which uses the image to dictate the spatial profile of the photoexcitation radiation delivered by projector 476. As in the alternative embodiment in which a scanning system is used, different wavelengths of light are used for image read-out and the resetting operation. Hence the image is erased in a fashion similar to the aforementioned scanning system embodiment. In a related embodiment, projector 476 may also be used as the source for the read out light of FIG. 11(a), thereby obviating the need to change the system configuration from that of FIG. 11(a) to that of FIG. 11(b). FIG. 11(c) shows the XLV in reset position, with liquid crystal director 480 returned to a substantially unperturbed arrangement.

After scanning the stored image in XLV 100 it is desirable to erase or reduce the residual electric field 132 produced by the trapped charges, shown in FIG. 3(c). As noted above, there are some known methods for optical resetting. However, it has generally been found that the existing methods do not produce a suitable level of ghost image reduction.

As noted above, it is to be understood that embodiments disclosed herein are not limited to XLV based imaging devices, and may be adapted to a wide range of blocking-type photoconductive imaging devices that employ various image readout methods. The foregoing discussion of a radiation detector to which the method is applicable is included merely as an example.

The preceding embodiments provided systems and method for resetting or erasing a blocking-type photoconductive imaging device using spatially dependent photoexcitation radiation that is absorbed in the photoconductive layer, where the spatial profile of the photoexcitation radiation is correlated with the spatial intensity of the residual image or charge density.

In other embodiments, as disclosed below, other systems and methods are provided for resetting a blocking-type photoconductive imaging detector having an electro-optic modulator, namely an x-ray light valve (XLV), where the resetting is performed by irradiating the electro-optic layer with photoionization radiation. Unlike the aforementioned embodiments involving photoexcitation of carriers in the photoconductive layer, selected embodiments provided below employ photoionization of mobile charge entities within the electro-optic layer, such that the mobile charges may neutralize the residual charges trapped at the interface of the electro-optic modulator layer and photoconductive layer. In the example embodiments provided below, the imaging devices employ a liquid crystal layer as the electro-optic layer. However, it is to be understood that the embodiments provided herein are not to be limited to liquid crystal electro-optic modulators, and that any suitable electro-optic modulator that includes photoionizable mobile charges may be employed.

Accordingly, in one example implementation, the imaging device is a liquid-crystal XLV device, as shown in FIGS. 1 and 2, the operation of which is illustrated in FIGS. 3(a) to 3(d). As described in detail above, XLV devices suffer from residual charges that are trapped at the interface of the electro-optic layer and the photoconductive layer. These residual charges produce ghost images and lead to a reduction in signal to noise and sensitivity. In one embodiment, the liquid crystal is substantially free of charges prior to the photoionization step.

Referring now to FIGS. 12(a) to 12(c), a method of resetting a liquid crystal based XLV device is illustrated, where trapped charges are neutralized or otherwise compensated via the photoionization of mobile charges in the electro-optic layer.

In FIG. 12(a), photoionization radiation 500 is directed in, and is substantially absorbed within, the liquid crystal layer. The photoionizing radiation 500 has a wavelength selected to photoionize a species within the liquid crystal layer and to generate oppositely charged mobile charged entities 505 within the liquid crystal layer 50. The mobile charge entities 505 may be, but are not limited to, electrons, holes, ions and charged molecules. The local electric field 520 produced by residual charges 515 then causes the mobile charged entities 505 to drift to either the electrode 36 or the interface 154.

Photoionization involves the removal of one or more electrons from a molecule or the dissociation of a molecule into ions (by the breaking of a bond such as a covalent bond) by absorption of visible or ultraviolet light. The parent molecule may be, for example, a liquid crystal molecule or impurity molecule that are typically otherwise neutral.

Without intending to be limited by theory, it is believed that photoionized mobile charged entities 505 drift under the influence of the residual electric field 520 and form layers of charges at the interfaces, thereby producing an opposing (screening) electric field indicated by dotted lines 510 in FIG. 12(b). The electric field within the bulk of the liquid crystal layer is thus greatly reduced, leading to the relaxation of the liquid crystal molecules thereby effectively erasing the image. Over time, the charges in each layer may neutralize or recombine by physical processes such as tunneling or thermal emission. The mobile charged entities are, thus, believed to be neutralized and returned to the bulk of the liquid crystal 50. It is to be understood that these interpretations of the physical processes are provided for heuristic purposes only and are not meant to limit the scope of the present disclosure in any way.

The screening of the residual field 520 and/or neutralization of the trapped charges 515 by the photoionized mobile charged entities 505 and opposing field 510 is believed to effectively result in the resetting of the XLV. The fluence of photoionizing beam 500 is selected to provide sufficient optical power to effectively neutralize at least a portion of the charges 515 trapped at the interface. The fluence may be selected to produce a substantially neutral device within minimal residual internal electric field and a substantially unperturbed director 525, as shown in FIG. 12(c). While the present disclosure describes photoionizing radiation 500 in terms of its fluence, it is to be understood that other related properties may also be controlled, such as, but not limited to, intensity, power, energy flux, irradiation time, and any combination thereof.

The photoionization process may be employed, for example, when the wavelength of the photoionization radiation overlaps with the absorption bands of the electro-optic layer, such as the liquid crystal material (and/or the absorption bands of impurities within the electro-optic layer), such that the absorption bands correspond to the photoionization of charged species. The suitability of the wavelength may be determined from ultraviolet-visible absorption spectrometry measurements of the liquid crystal layer. In one example implementation where the electro-optic modulator is a liquid crystal, the optical source may have a wavelength within the range of 200 to 400 nm, where the absorption bands corresponding to photoionization processes in liquid crystals are expected to lie.

Suitable sources for generating the photoionization radiation include, but are not limited to, lasers, light emitting diodes, incandescent light sources, and fluorescent lamps. The light source may be optically filtered to deliver a desired spectral content for photoionization.

Figure 13:
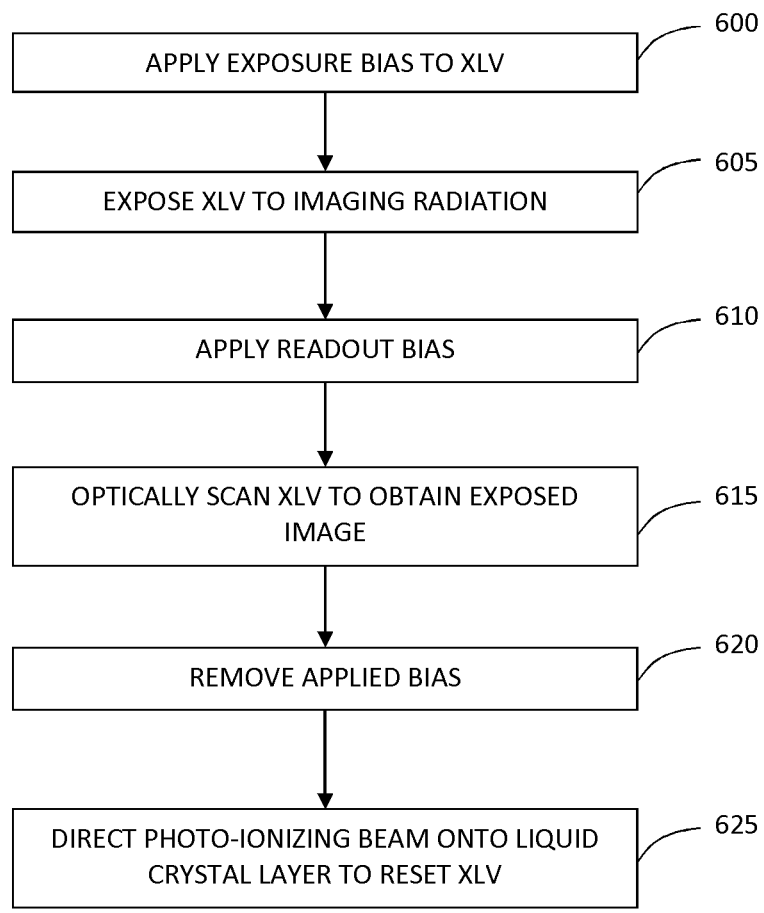
FIG. 13 provides a flow chart illustrating a method of erasing an image in an XLV via photoionization in the liquid crystal layer.

FIG. 13 provides a flowchart that illustrates the aforementioned method of obtaining an image and resetting an XLV imaging detector for a subsequent measurement. In step 600, prior to obtaining an image, an exposure bias potential is applied to the electrodes of the XLV imaging device. The object is then placed in front of the detector plane, and the detector is exposed to x-rays in step 605. The exposure of the x-rays creates trapped charges at the interface between the photoconductive and liquid crystal layers, as illustrated above in FIG. 3.

In step 610, a readout bias potential is applied to the device, and in step 615, the imaging detector is optically interrogated (scanned or directly imaged) and the image is obtained based on the intensity of the optical signal reflected from the interface. The readout bias is then removed in step 620.

Figure 12:
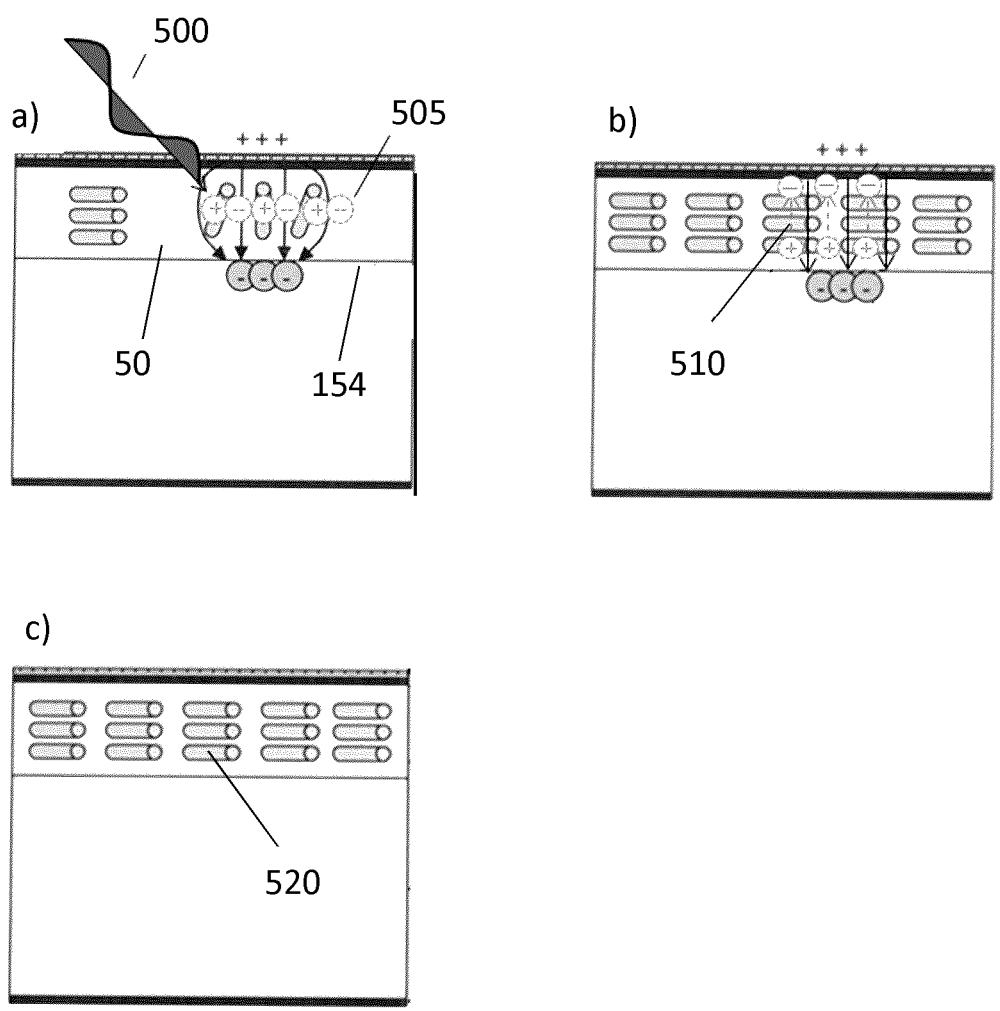
FIGS. 12(a)-(c) illustrate a method of resetting an XLV using photoionizing radiation that is absorbed within the liquid crystal layer.

In step 625, the photoionization radiation is directed onto the liquid crystal layer to reset the device and improve the signal-to-noise ratio of subsequent measurements. As illustrated in FIG. 12, the photoionization radiation photoionizes species within the liquid crystal layer, such as liquid crystal molecules or impurity molecules, and the resulting mobile charged entities drift and screen the residual field within the liquid crystal layer.

The fluence of the photoionization radiation is selected to at least partially reset the imaging detector. A suitable intensity or fluence may be obtained by a calibration step, in which the effect of varying fluences of photoionization radiation is measured, and the fluence producing a desired degree of resetting is selected. In one example, a suitable full scale fluence for photoionizing an XLV imaging device with a photoionization radiation source having a wavelength of 340 nm is approximately 120 microJoules per square millimeter.

The photoionization radiation may be provided via an optical system that substantially uniformly illuminates the imaging detector, for example, as a broad beam or as diffuse illumination. Alternatively, a photoionizing beam may be scanned across the surface of the XLV imaging device in a serial manner.

Although the preceding embodiments involving the use of photoionizing radiation have been disclosed without requiring any spatial dependence or manipulation of the photoionizing radiation, it is to be understood that the spatial intensity or fluence of the photoionizing beam may be determined based on the intensity of the recorded image, in a manner similar to the methods disclosed in the preceding embodiments involving the application of photoexcitation radiation for image erasure.

For example, the method of erasure may include the steps of determining, based on the measurement image (or a residual image), a prescribed spatial fluence profile for the photoionization radiation, such that when the photoionization radiation is directed into the liquid crystal with the spatial fluence profile, a spatially-dependent concentration of mobile charge entities are generated for locally reducing an effect of the trapped charges. The photoionization radiation may then be directed into the liquid crystal with the prescribed spatial fluence profile in order to achieve resetting of the imaging device.

The aforementioned calibration procedures for determining the appropriate spatial fluence profile of the photoexcitation radiation may be applied to determine calibrate and this determine an appropriate spatial fluence profile for the photoionization radiation.

The preceding embodiments have provided methods for resetting an XLV imaging detector by photoionizing mobile charge entities in the electro-optic modulator layer. In an additional embodiment, photoionizing radiation may also be employed to pre-condition the electro-optic modulator prior to the measurement of an object using imaging radiation.

An example of such an embodiment is illustrated in FIGS. 14(a) to 14(c), in which the application of photoionizing radiation to the liquid crystal layer 50 of an XLV device prior to an image acquisition step is shown. In FIG. 14(a), an XLV device is shown as being pre-conditioned by the application of a pre-conditioning bias potential 700. The pre-conditioning bias potential, which is typically large relative to the readout bias potential, causes the liquid crystal director field to align with applied field 705.

In order to reduce or eliminate this tendency for the liquid crystal director field to be perturbed or aligned by the pre-conditioning bias potential 700, photoionizing radiation 710 is directed onto the liquid crystal layer 50. Photoionizing radiation 710 is shown in FIG. 14(b) as being rapidly absorbed within liquid crystal layer 50, whereby oppositely charged entities 715 are generated via a photoionization process.

As shown in FIG. 14(c), charged entities 720 and 725 separate under the action of applied bias potential 700 and act to internally screen the applied bias potential. Accordingly, the effect of the pre-conditioning bias potential 700 is markedly reduced, and the liquid crystal is maintained in a more native state. The step of directing photoionizing radiation onto the liquid crystal may therefore be employed both during pre-conditioning (prior to imaging), and during an erasure step (post-imaging).

In one embodiment, shown in FIGS. 14(d) to 14(f), the applied bias potential 700 is not removed between the successive steps of pre-conditioning, exposure to imaging radiation, and read-out. For example, the initially applied bias potential may by 5000V, which may be maintained through steps 14(*a*) through 14(*d*).

In order to overcome the threshold field of the liquid crystal cell, the applied bias potential may be slightly increased in step 14(*e*). Accordingly, the applied bias potential may be increased relative to the initial applied bias by an amount sufficient to generate an electric field within the liquid crystal layer for overcoming the threshold field. For example, one may consider a device with a photoconductor thickness of 1000 microns, a liquid crystal layer of 5 microns, and a threshold potential across the liquid crystal of 1 V. As described above, a voltage increase of 201 V is required to overcome the threshold. Accordingly, if the initially applied bias potential is 5000 V, and this potential is screened via the creation of mobile charges within the liquid crystal layer, then the voltage may be increased during readout to 5201 V. Having applied an appropriate readout bias potential increase, the liquid crystal layer 50 may be optically interrogated as shown in FIG. 14(*d*).

Figure 14:
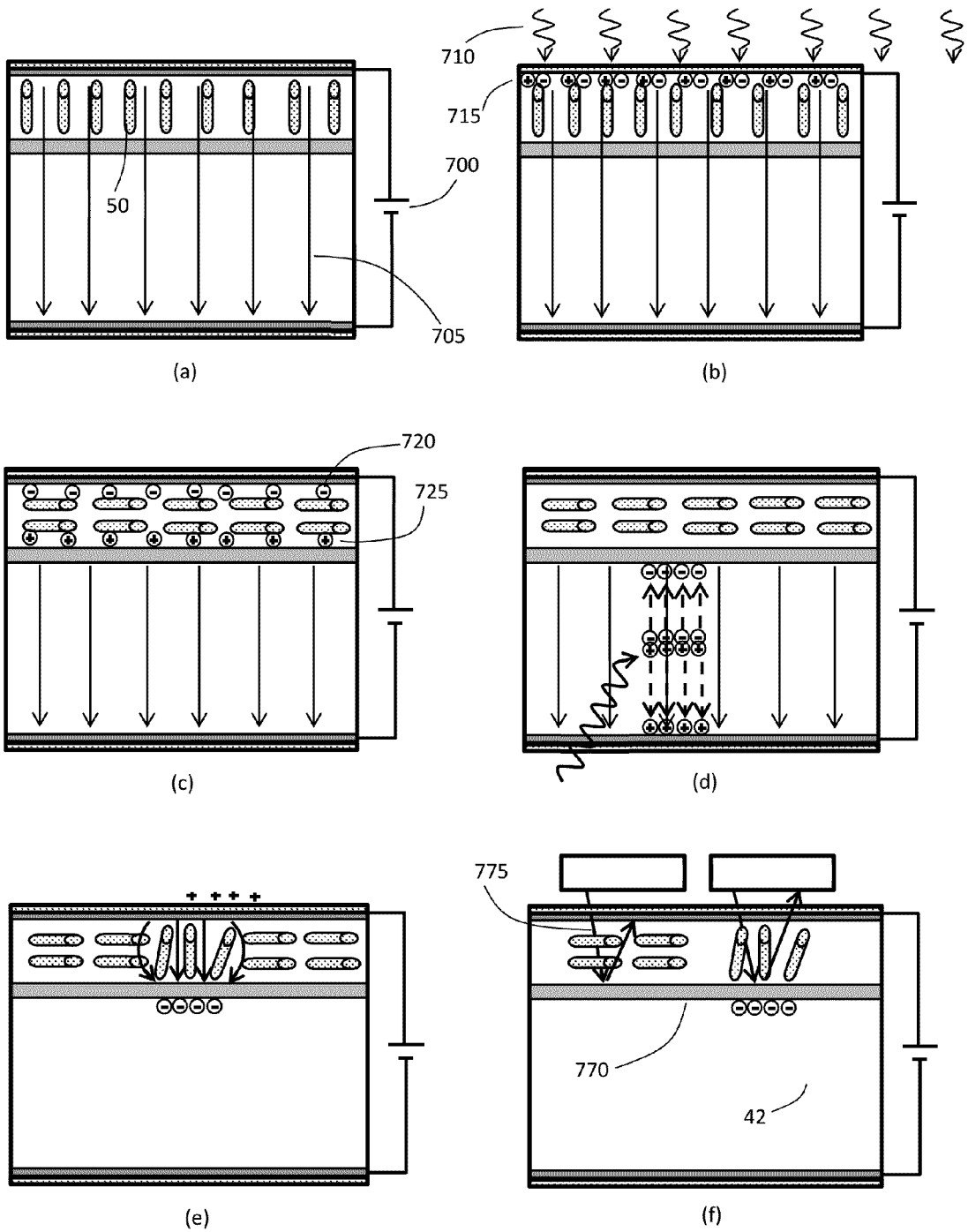
FIG. 14 schematically illustrates the steps in employing photoionization radiation for reducing the internal field within the liquid crystal layer during a pre-conditioning step prior to measuring an image.
Figure 15:
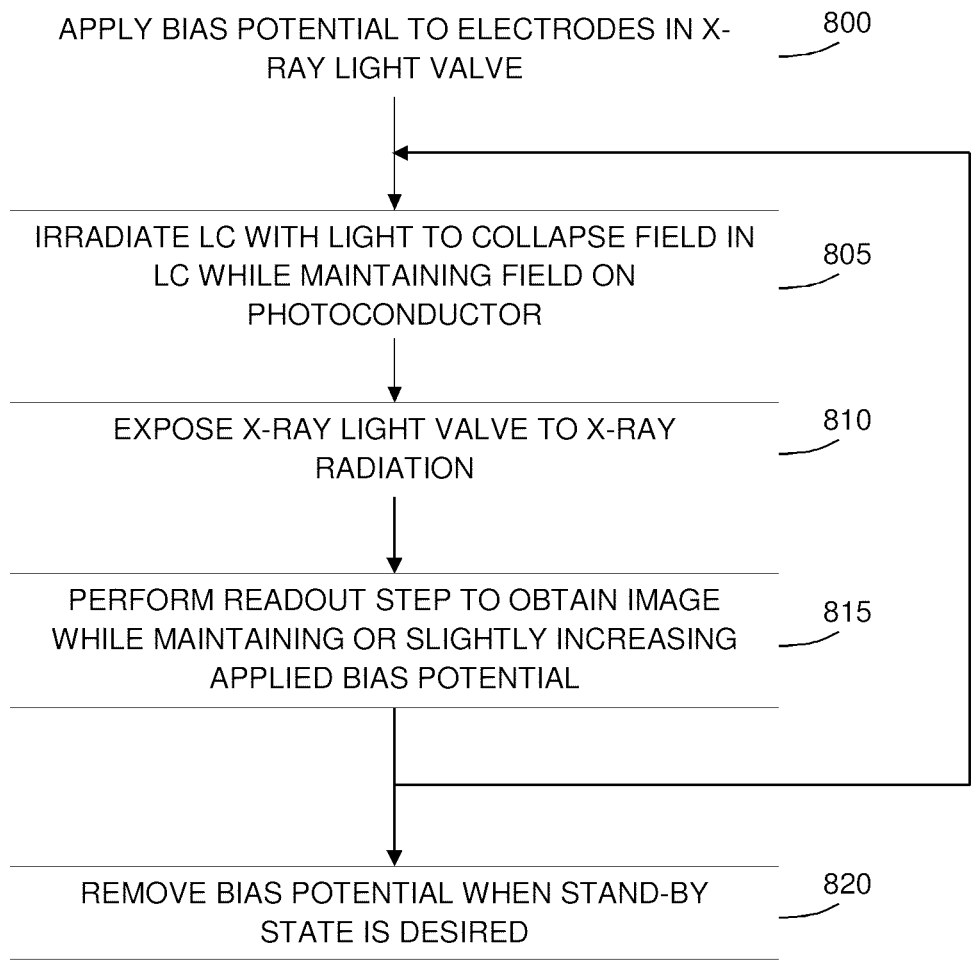
FIG. 15 provides a flow chart illustrating the steps in preconditioning an XLV involving the irradiation of the liquid crystal layer with photoionization radiation.

These steps are further illustrated in the flow chart provided in FIG. 14, where in step 800, an initial bias potential is applied to the XLV prior to an imaging step. In step 805, the liquid crystal layer is irradiated with photoionizing radiation, thereby generating mobile charged species internally within the liquid crystal layer that screen or collapse the internal field, effectively removing the effect of the applied bias potential on the liquid crystal layer. The imaging device may then be exposed to x-ray imaging radiation in step 810 and a measurement may be obtained.

In step 815, the bias potential may be slightly increased in order to raise the internal field within the liquid crystal layer above that of the threshold value. After having increased the electric field in the liquid crystal layer above threshold, the stored charge image may be optically measured.

If the imaging device is to be used for repeated imaging exposures within a given time frame, the present embodiment may be performed without removal of the applied bias potential by repeating steps 805 to 815 each time an image is to be measured. Accordingly, photoionizing step 805 effectively plays a dual role of maintaining a low internal electric field within the liquid crystal layer during pre-conditioning, while also erasing any residual image, as per the embodiments described above. This embodiment may also be useful in reducing the cycle time of the imaging device, and reducing an inrush of dark current while performing successive method steps, since the applied voltage is maintained at a near constant level. Finally, as shown in step 820, when the imaging device is left in stand-by mode, the bias potential may be removed.

Figure 16:
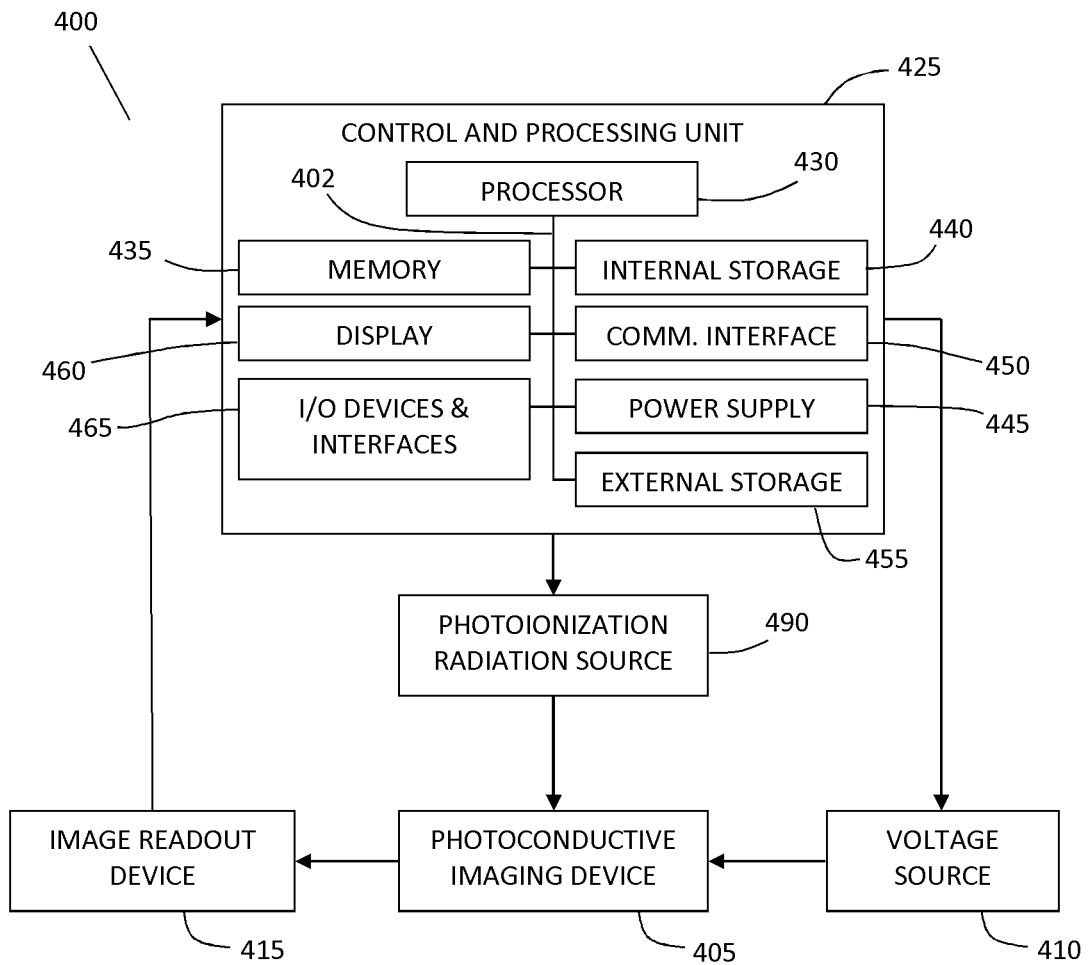
FIG. 16 provides a block diagram of an XLV imaging system including a source of photoionization radiation.

FIG. 16 provides a schematic of a system for performing x-ray detection using an XLV apparatus that is resettable via a photoionization source. System 400 includes a photoconductive imaging device 405, voltage source 410 (for applying a forward bias across imaging detector 405 while performing an imaging step, and a reverse bias during a resetting operation as described above), image readout device 415, photoionization radiation source 490, and control and processing unit 425. Details of each component of the system have been described above.

In another embodiment, an x-ray light valve imaging device includes a spectrally selective intermediate layer between the opto-electronic modulator layer and the photoconductive layer (i.e. a layer having wavelength dependent or spectrally varying transmission). The spectrally selective layer transmits light of a first wavelength or wavelength range while absorbing, reflecting, scattering or diffracting light of a second wavelength or wavelength range, such that the transmission of light within the second wavelength range into the photoconductive layer is substantially reduced. The first wavelength range or the second wavelength range may span a single spectral region, or may include two or more spectral regions. For example, if the spectrally selective layer includes an optically absorbing material, then the second wavelength range may include one or more absorption bands. In one example, spectrally selective layer may be a spectrally selective mirror, such as a dielectric mirror, or a dielectric mirror with one or more absorbing layers or materials.

One embodiment is illustrated in FIG. 14, where spectrally selective layer 770 is employed in part as a reflector for readout light 775. Spectrally selective layer 770 may also spectrally reflect, absorb, scatter or diffract photoionization radiation 710, such that the excitation of charges by photoionization radiation 710 is substantially limited to the photoionization of mobile charge entities in liquid crystal 50, and not photoexcitation within photoconductive layer 42.

Spectrally selective layer 770 may be conductive, semiconducting, or insulating. In one embodiment, spectrally selective layer 770 is conductive, whereby charge transfer across spectrally selective layer 770 is possible. Such an embodiment may be advantageous, for example, when employing photoionization within the liquid crystal layer for erasure of an x-ray light valve imaging device, where charge transfer across spectrally selective layer 770 allows for recombination of trapped charges and photoexcited mobile charged entities.

Figure 17:
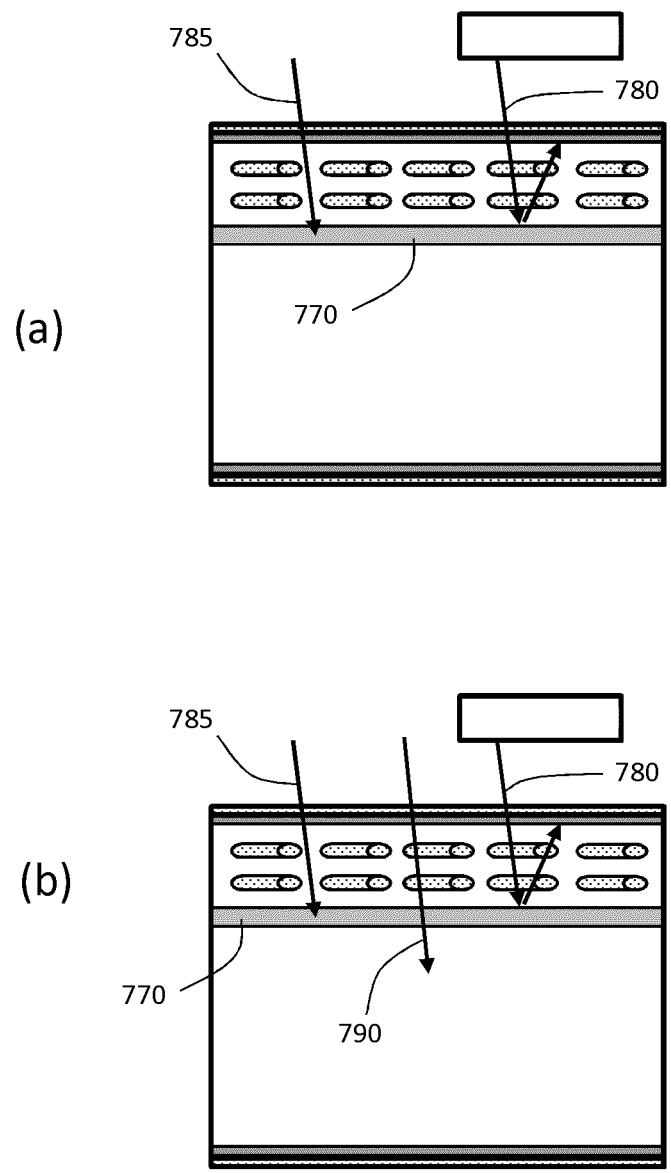
FIG. 17 illustrates an XLV imaging device including a spectrally selective layer.

FIG. 17(*a*) provides an example implementation of an x-ray light valve imaging device in which spectrally selective layer 770 reflects readout light 780 having a wavelength $\lambda_1$ and absorbs photoionization radiation 785 having a wavelength $\lambda_2$, such that photoionization radiation is substantially prohibited from entering photoconductive layer 42.

In FIG. 17(*b*), another embodiment is shown in which spectrally selective layer 770 reflects readout light 780 having a wavelength $\lambda_1$ and reflects or absorbs photoionization radiation 785 having a wavelength $\lambda_2$, such that photoionization radiation is substantially prohibited from entering photoconductive layer 42. In addition, however, spectrally selective layer 770 also transmits photoexcitation radiation 790 having a wavelength $\lambda_3$, such that photoexcitation radiation 790 is permitted to enter photoconductive layer 42. Such an embodiment permits image erasure and/or pre-conditioning of the device from a single side of the device.

Although the spectrally selective layer 770 is described in terms of its spectral nature, the layer may also exhibit polarization dependent transmission, such that the polarization state of the incident light enables further control over the transmission of light through the layer.

In one example implementation, spectrally selective layer 770 may include one or more of spectrally selective light absorbing pigment particles, light scattering particles, and electrically conductive particles. This layer may be formed on the semiconductor interface by, for example, settling from a solution or suspension in either an aqueous or organic solvent. In another fabrication approach, this layer could be spin coated.

The layer may further include a binder, whose purpose is to stabilize and bind the components into a permanent structure. The binder could also be a material with an appropriate level of electrical conductivity to prevent the buildup of charge. The binder could also incorporate a soluble dye to provide light absorption of selected wavelengths (in addition, or as an alternative, to the pigment particles). The resulting deposited layer may be air dried or with vacuum assistance along with modest amounts of heating to prevent damage to the photoconductor layer. In a variation of this approach, the conducting particles may also provide spectrally selective absorption.

In yet another embodiment, spectrally selective layer 770 may include two or more sublayers with differing amounts of each component in each of the sublayers. For example, in an embodiment including both scattering particles and spectrally selective light absorbing particles, the scattering particles may be provided with higher concentration in the sublayers that are closer to a light source, while the spectrally selective light absorbing particles could be provided in higher concentration in sublayers that are closer to the photoconductor layer.

The following examples are presented to enable those skilled in the art to understand and to practice embodiments of the present disclosure. They should not be considered as a limitation on the scope of the present embodiments, but merely as being illustrative and representative thereof.

EXAMPLES

Example 1

Photoionization Current Dynamics and Charge Species Determination

In the present example, results are provided from experimental studies designed to explore the nature of photoionization and charge dynamics within a liquid crystal layer. As shown below, the studies described herein illustrate that mobile charge pairs can be readily photoionized within a liquid crystal cell and transported across the cell.

To perform a resetting operation in an XLV using photoionization within the liquid crystal layer, the minimum amount of charge required in liquid crystal depends on the amount of trapped charges at the photoconductor/liquid crystal interface. In the present example, the photoconductor is taken to be a-Se, and the amount of trapped charges in the a-Se is estimated by simulating a mammographic condition. The x-ray tube is modeled to operate at 28 kV and at a distance of 0.6 meter from the breast, emitting x-ray energy spectrum in the mammographic[5] range with peak at 17 keV. The thickness of aluminum filter for x-rays is 0.3 mm, and the breast composition is modeled as H(0.106)C(0.332)N(0.03) O(0.527)Na(0.001) P(0.001)S(0.002)Cl(0.001), with a density of 1.02 gm/cm$^3$.

During imaging, x-rays pass through the breast phantom into the a-Se of thickness L=200 μm and create electron hole pairs. An attenuation coefficient (μ) in Se from simulations is employed to calculate quantum efficiency[5], with $Q_e=1-\exp(-L\mu)$, as a function of x-ray quanta energy. Quantum efficiency multiplied by number of incident photons gives number of absorbed photons in a-Se. The sum of number of photons absorbed multiplied by corresponding energy gives total energy (E) absorbed inside a-Se.

The total energy (E) absorbed in a-Se divided by the energy necessary to generate an electron-hole pair (40 eV) in a-Se gives total number of charges as N=5.47×10$^8$/mm$^2$ that are created in the a-Se detector. This is the amount of charge responsible to create a field in liquid crystal cell, if all of the charges were transported across the Se, in an ideal situation. Therefore, according to the present simulations, the minimum amount of charge required in liquid crystal to balance the field of trapped charge in order to reset the XLV is N=5.47×10$^8$/mm$^2$. The trapped charges of this amount generate a potential difference of 4.0 V across a liquid crystal cell of thickness 5 μm and capacitance of 0.54×10$^{-9}$ F.

After estimating the minimum amount of charge required in liquid crystal, the amount of light energy required to create this amount of charges in a liquid crystal is estimated. This is achieved by performing a photoconductivity experiment in a liquid crystal. The photoconductive property implies that the substance should be able to generate charge by light and support the transport of the photoexcited charges. Accordingly, photoconductivity involves: light absorption, charge carriers generation, charge carriers separation and transport.

Figure 18:
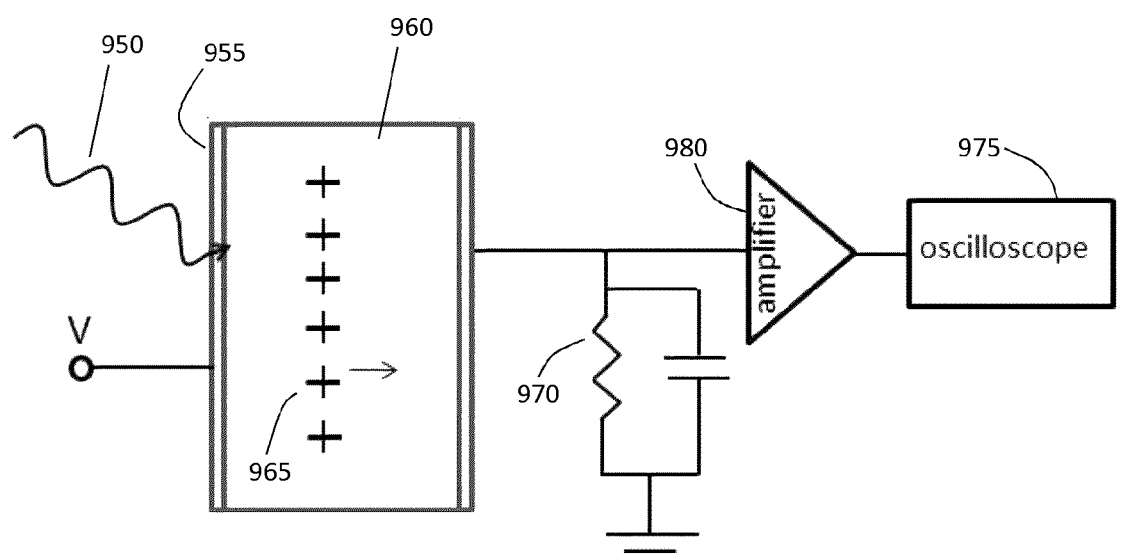
FIG. 18 illustrates the experimental setup for time of flight measurements in liquid crystal sandwiched between two electrodes, where a photogenerated charge sheet moves through the sample to produce a pulse of voltage signal across the external resistor which is recorded by an oscilloscope.

The charge transport ability of the material is stated in terms of mobility, defined as $$\mu = L/(E\tau), \qquad (1)$$

where L is the distance traveled by the charge carrier in during the transit time, τ, of charge carriers under applied field E. The general experimental scheme is illustrated in FIG. 18. A laser pulse 950 is incident on the front transparent electrode 955 (ITO) and passes into the liquid crystal 960. The liquid crystal material 960 absorbs photon energy and creates charge pairs. Charges so produced move towards the electrodes of opposite polarity. If it is assumed that light is strongly absorbed within a small thickness of the material, δ<<L, a member of the charge pair is quickly absorbed by the irradiated electrode while the another member forms a small sheet of charge 965 and drifts towards the opposite electrode due to external field. This drift of the charge sheet creates potential difference across the external resistor 970 until charge sheet reaches to the opposite ends. The resulting signal is recorded in an oscilloscope 975 after amplification by amplifier 980. The shape and width of the photocurrent pulse gives the information about the conductivity of the material and the transport mechanism. The liquid crystal cell was filled with liquid crystal (Merck E7) by capillary action at room temperature.

The transient photocurrents were measured by the conventional time-of-flight method using N2 laser (λ=337 nm and pulse duration 800 ps) as excitation light and recorded by digital oscilloscope (Tektronix 2.5 GHz, 20 GS/sec). The bias voltage was applied to the sample using high power supply unit (Keithley 237). The wavelength for photoionization was chosen based on an ultraviolet-visible light spectrometry experiment (Spectrometer: Synergy 4-Biotek). The results were analyzed using Matlab™. The transit time, τ, of charge carriers was determined from the kink point of the transient photocurrent measured.

Figure 19:
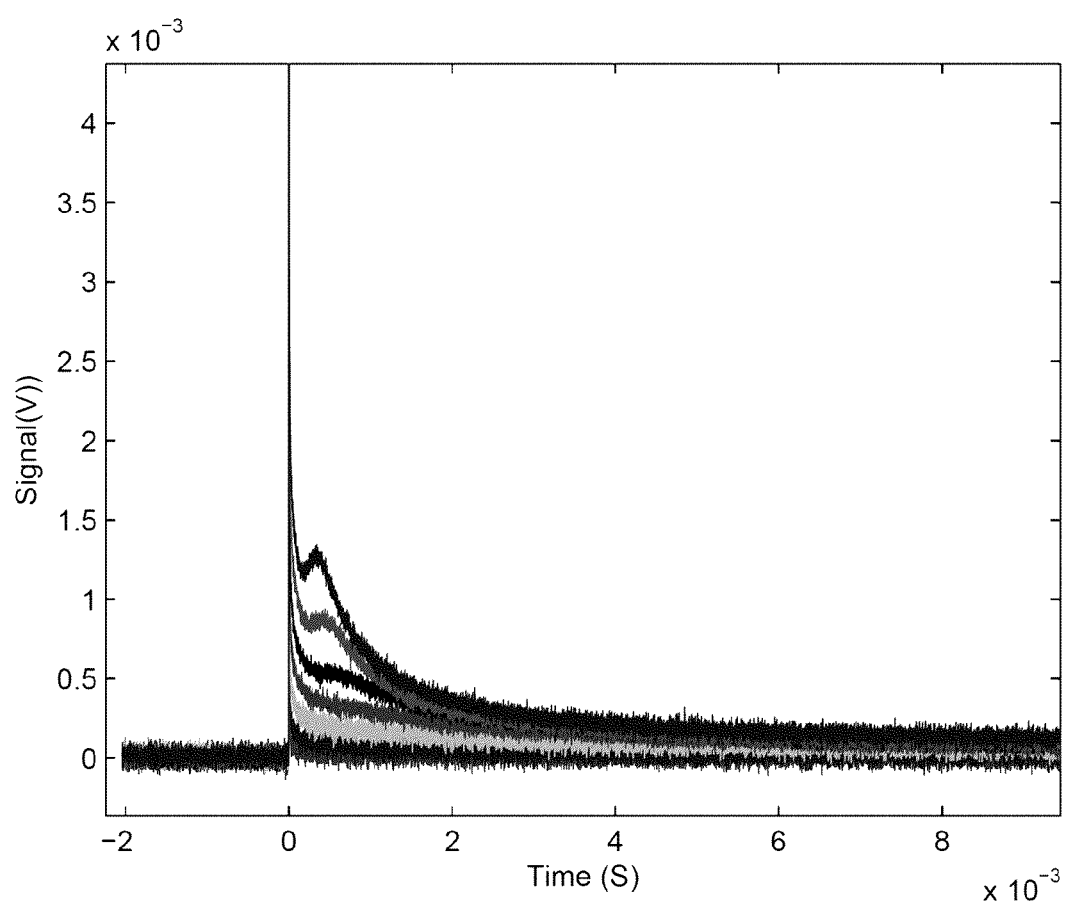
FIG. 19 shows the measured photovoltage signal of positive charge carriers in E7 at room temperature for applied voltages from 20 volts to 90 volts going from bottom to top.

The voltage signal at room temperature in nematic phase of E7 is shown in FIG. 19 for positive applied voltages from 20 volts to 90 volts and laser energy of 16 μJ. The initial fast decay of signal indicates the extinction process of the photogenerated charges. The extinction of charge may be either due to recombination or by trapping at deep traps arising from the impurities, or structural defect. The horizontal plateau (in some traces) arises because of the transport of the charge sheet across the sample. The long tail of the signal is believed to arise due to the slow dribble of charge carriers trapped in the shallow traps.

Figure 20:
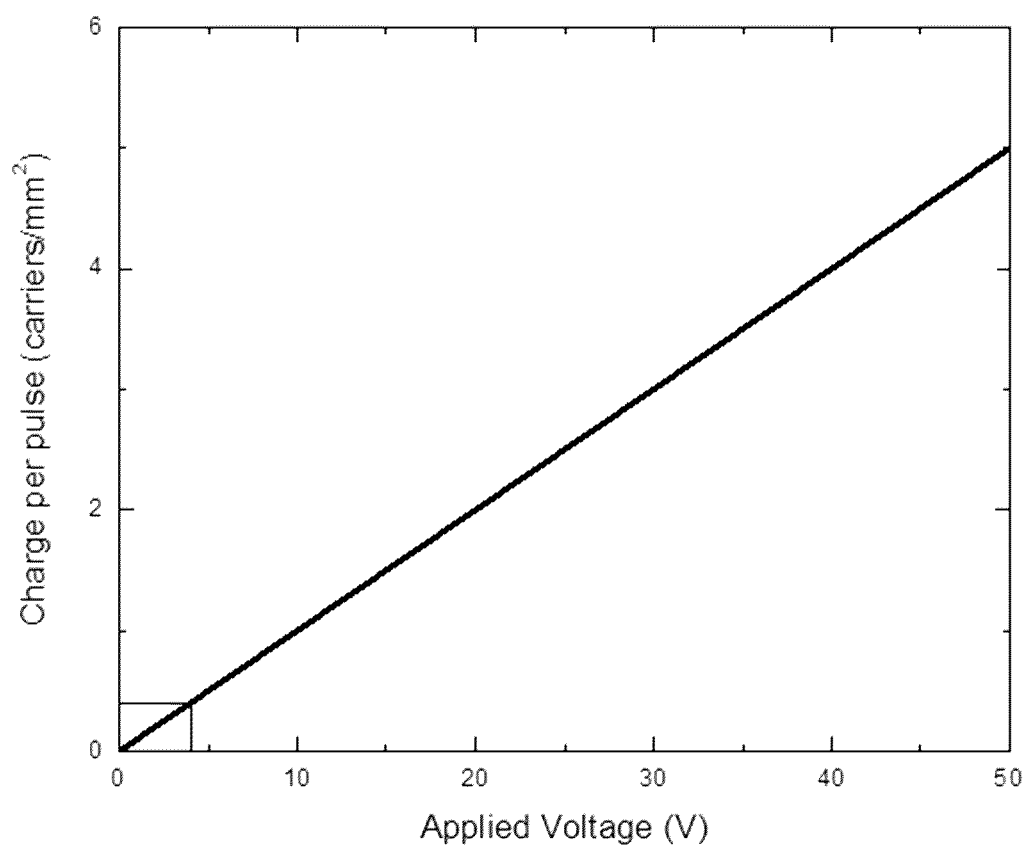
FIG. 20 plots the amount of charge carriers generated by the laser in the liquid crystal at a given voltage.

Each curve was separately integrated to calculate the number of charge carriers generated by laser in the liquid crystal at a given voltage. This is illustrated schematically in FIG. 20. For example at 4V the number of elementary charges generated by the laser with an output of 21.3 μJ per pulse incident on a 25 mm$^2$ area is approximately 4.0×10$^8$/mm$^2$ per pulse. This is comparable to the charge 5.47×10$^8$/mm$^2$ required in liquid crystal to balance the field of trapped charge generated from an x-ray exposure.

Figure 21:
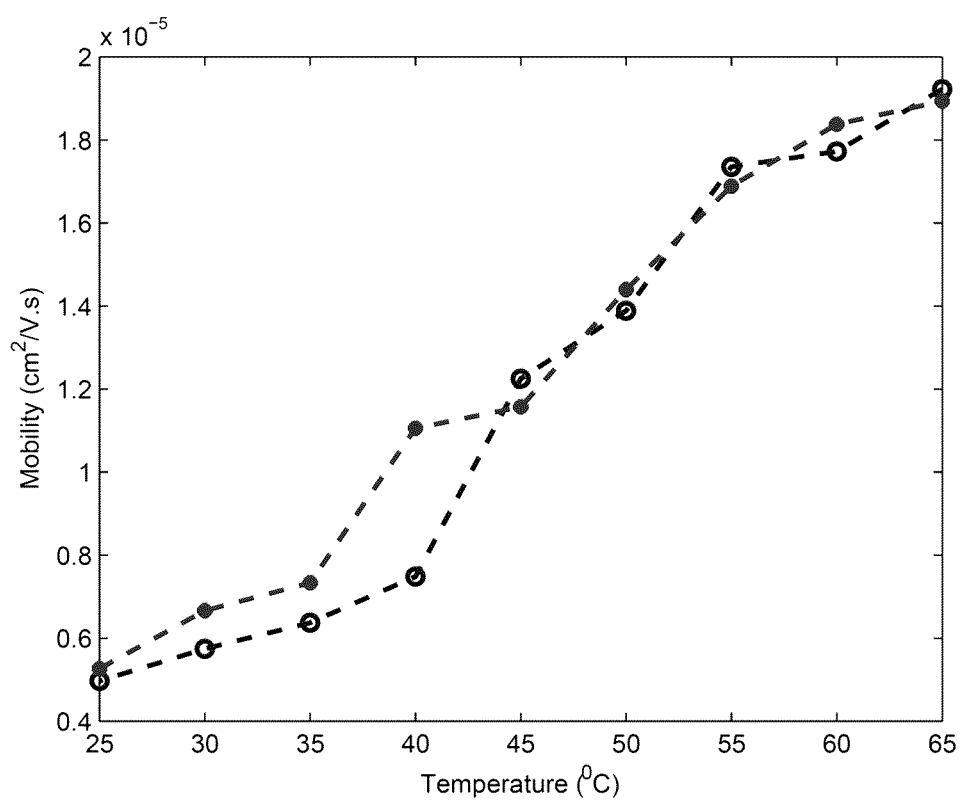
FIG. 21 plots mobility as a function of temperature at 40 (closed circles) and 50 (open circles) volts.

The mobility was calculated and the transport mechanism was analyzed in terms of whether it is electronic or ionic. The transit time was calculated from the kink in the plateau from where signal starts to decreases. The mobility is calculated by using equation (1) where the sample thickness is L=5 µm, and plotted in FIG. 21. The mobility is in the order of $10^{-6}$ cm²/V·s Taking account of low mobility, it is likely that carrier transport may be ionic. The ionic transport is a probable mechanism of charge transport in nematic liquid crystals because of the low viscosity. In order to clarify whether transport mechanism is ionic or electronic the carrier transport was studied as a function of temperature. It was found that mobility increases with temperature. As the temperature increases, the viscosity of the medium decreases, offering less resistive path to the ionic charge resulting in an increase in mobility. On the other hand increase of the temperature increases the intermolecular distance thereby increasing the hopping distance for electronic conduction resulting in a decrease in mobility. It was therefore concluded that the charge transport mechanism is likely ionic. This is supported also by the estimation of the viscosity from Walden's rule which is valid for ionic transport and expressed by $\mu\eta=e/6\pi r$ where $\eta$ is the viscosity of the medium and r radius of the ion. Assuming the ionic radius of E7 to be 0.5 nm, a value close to literature value[6], the observed mobility µ at 20° C. of $4\times10^{-6}$ cm²/V·s yields $42.5\times10^{-3}$ Ns/m² for viscosity $\eta$. This is quite close to the viscosity of E7 given in data sheet by Merck.

Example 2

Figure 22:
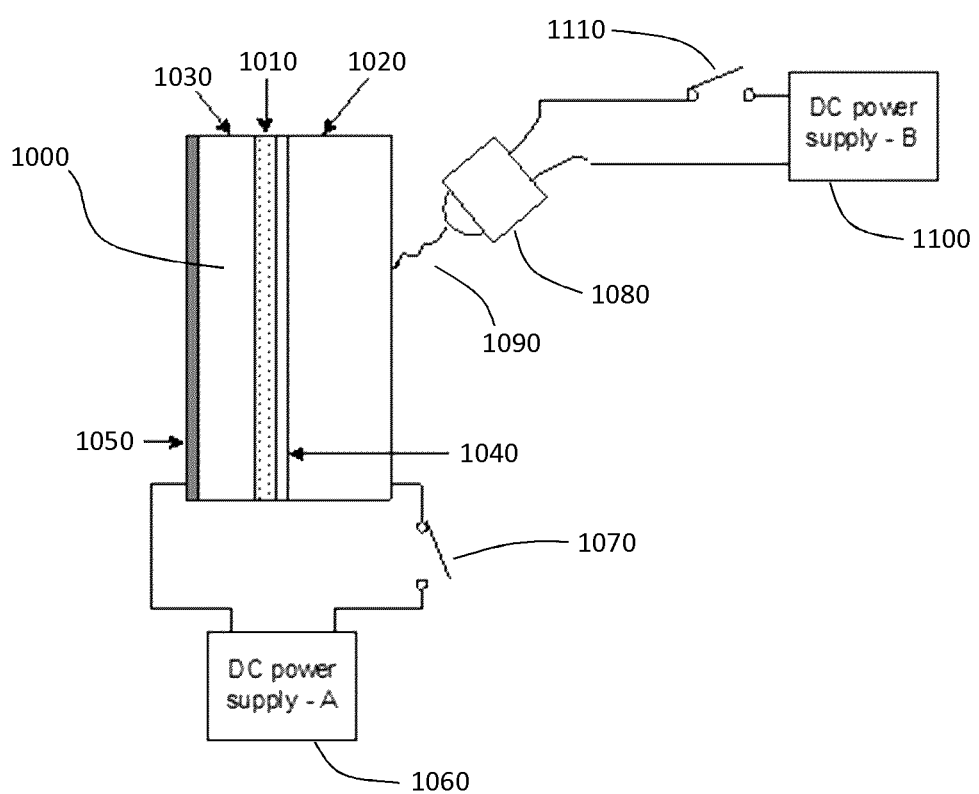
FIG. 22 shows the experimental apparatus employed for demonstrating the effect of photoionization radiation on a liquid crystal cell.

Demonstration of Compensation of Stored Charge in a Liquid Crystal Layer by Means of UV Exposure In the present example, the resetting of a liquid crystal cell via the application of photoionization radiation is demonstrated. FIG. 22 shows the experimental setup for the measurement. The cell 1000 consists of a liquid crystal (LC) layer 1010 sandwiched between two glass substrates 1020 and 1030. One glass substrate 1020 is 0.4 mm thick and coated with a transparent, electrically conducting layer 1040 of Indium-Tin-Oxide (ITO) with the ITO side in contact with the LC. The other glass substrate 1030 is 60 microns thick and is coated in stripes with a reflective metallic conducting layer 1050. Here the glass side is in contact with the LC layer 1010 and the metal coating faces the outside. An electrical bias may be applied to the structure by means of an external DC power supply 1060 connected between the ITO and one of the metal stripes. The power supply can be interrupted by a switch 1070, leaving the cell electrically floating.

An ultraviolet LED 1080, model UVTOP335, from Sensor Electronic Technology, is placed in the vicinity (~2 or 3 cm) of the cell 1000, on the ITO side, and is capable of shining UV light 1090 on the LC layer 1010 through the glass substrate 1020. The wavelength of the LED is typically 340 nm and its typical output power is 400 microwatt. The LED may be powered by power source 1100 and controlled by switch 1110. The cell was illuminated on the ITO side by red light and the reflection was viewed by a digital camera (not shown in the figure).

Figure 23:
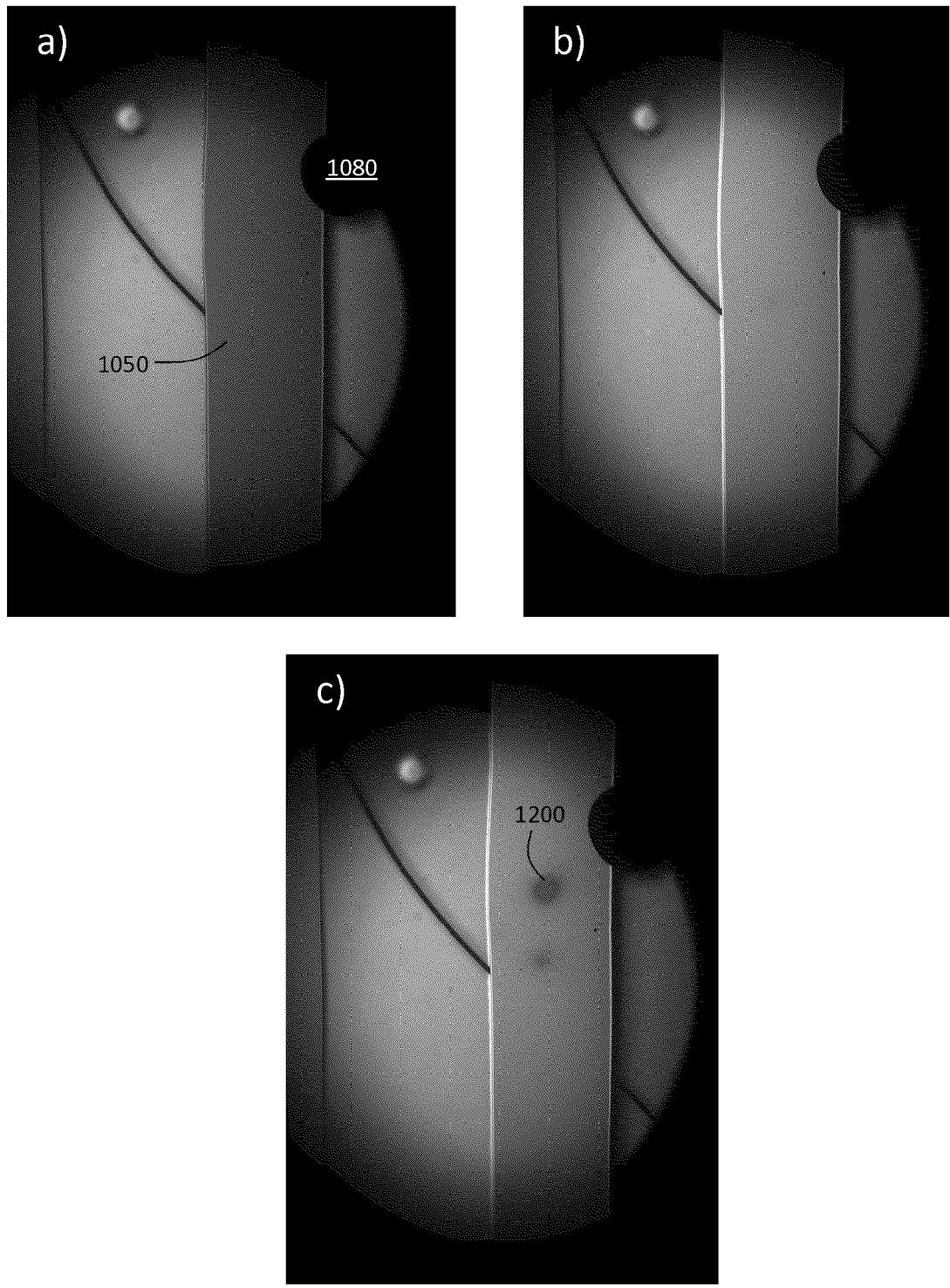
FIG. 23 shows photographs of (a) a liquid crystal cell in the off state, (b) a liquid crystal cell in the on state, and (c) a liquid crystal cell after photoionization radiation has been applied to selected regions.

FIGS. 23 (a)-(c) show the cell from a top view, looking through the top ITO layer into the liquid crystal cell. Metal contact 1200 is provided on the bottom of the cell and is visible through the transparent cell. Accordingly, the application of a potential bias between the top ITO contact and bottom metal contact 1200 causes the liquid crystal region above bottom metal contact 1200 to experience an applied electric field. A UV LED 1210 is provided above the cell for illuminating the cell through the ITO contact.

Initially the cell is unbiased and in its dark state, as shown in FIG. 23(a). The cell is then biased with 10 volts DC while keeping the UV LED switch in the off position. This brings the cell to its bright state as seen in FIG. 23(b).

The cell bias is removed leaving the cell electrically floating. The bright state is retained since charge is still stored on the cell's capacitance (~1500 pF). The UV LED is then turned on for 3 seconds. The area 1200 of the cell illuminated by the LED reverts to the dark state as in the unbiased condition, as seen in FIG. 23(c).

The observation that the area 1200 illuminated by the LED reverts to the dark state, as in the unbiased condition, demonstrates that charge has been generated in the LC layer 1010 by the UV illumination, and that the generated charge is in sufficient amount to neutralize the field from the applied bias. As an XLV structure experiences similar amounts of stored charge, these results indicate that an erasure procedure based on this principle is achievable.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

REFERENCES

[1] I. Koprinarov, and et. al., Med. Phys. 34, 4609, (2007).
[2] D. MacDougall, and et. al., Proc. Of SPIE 6510, 651018-1, (2007).
[3] C. Liu, and et. al., Chem. Mater. 9, 1422, (1997).
[4] C. Liu, and et. al., Chem. Mater., 10, 840, (1998).
[5] S. Kasap and et. al. Phys. Status. Solidi B, 246(8):1794, 2009.
[6] S. Murakami, H. Nitio, and M. Okuda. J. Appl. Phys., 78:4533, 1995.

Therefore what is claimed is:
1. A method of erasing a residual image from a blocking-type photoconductive imaging device, the blocking-type photoconductive imaging device including a photoconductive layer, the method comprising the steps of:
    a) measuring the residual image;
    b) providing a photoexcitation radiation source for generating photoexcitation radiation with a wavelength suitable for photoexciting electron-hole pairs within the photoconductive layer;
    c) determining a prescribed spatial fluence profile for the photoexcitation radiation, wherein the prescribed spatial fluence profile is spatially correlated with the residual image such that when the photoexcitation radiation is directed into the photoconductive layer with the prescribed spatial fluence profile:
        the photoexcitation radiation received at a given spatial location in the imaging detector is related to the intensity of the residual image at the given spatial location, and
        a spatially-dependent concentration of electrons and holes are generated for locally reducing an effect of trapped charges located at or near an interface of the photoconductive layer;
    d) applying a reverse bias potential to the imaging device, the reverse bias potential having a polarity opposite to that of a previously applied exposure bias potential; and
    e) directing photoexcitation radiation with the prescribed spatial fluence profile into the photoconductive layer while applying the reverse bias potential, such that photoexcited electrons or holes drift towards and recombine with the trapped charges.

2. The method according to claim 1 wherein the step of directing the photoexcitation radiation into the photoconductive layer includes directing the photoexcitation radiation into the imaging device from a side that is closest to the interface.

3. The method according to claim 2 wherein a wavelength of the photoexcitation radiation is selected such that a substantial portion of the photoexcitation radiation is absorbed adjacent to the interface.

4. The method according to claim 1 wherein a fluence of the photoexcitation radiation at a given spatial location, when directed onto the imaging device, is related to an intensity of the residual image at a corresponding spatial location according to a monotonic relationship.

5. The method according to claim 4 wherein the monotonic relationship includes at least a range wherein the relationship is substantially linear.

6. The method according to claim 1 wherein a fluence of the photoexcitation radiation at a given pixel in the imaging device is proportional to an intensity of the residual image at the given pixel.

7. The method according to claim 1 wherein the step of directing the photoexcitation radiation with the prescribed spatial fluence profile into the photoconductive layer includes scanning the photoexcitation radiation over the imaging device.

8. The method according to claim 1 wherein the step of directing the photoexcitation radiation with the prescribed spatial fluence profile into the photoconductive layer includes imaging the photoexcitation radiation onto the imaging device.

9. The method according to claim 1 further comprising the steps of:
   f) re-measuring the residual image; and
   g) determining if a suitable level of erasure has been achieved.

10. The method according to claim 9 further comprising repeating steps c) through g) one or more times until a suitable level of erasure has been achieved.

11. The method according to claim 1 wherein the step of determining, based on the residual image, the prescribed spatial fluence profile for the photoexcitation radiation includes the step of employing previously determined calibration data relating image intensity to photoexcitation radiation fluence.

12. The method according to claim 11 wherein the calibration data is obtained according to the steps of:
   i) measuring a reference image of a reference object;
   ii) selecting a full-scale fluence of photoexcitation radiation for image erasure;
   iii) performing image erasure according to steps a) to e) employing the selected full-scale fluence;
   iv) determining a level of image erasure of the reference image;
   v) repeating steps i) to iv) for different full-scale fluence values; and
   vi) selecting an appropriate full-scale fluence value for obtaining a sufficient level of image erasure.

13. The method according to claim 11 wherein the calibration data is obtained according to the steps of:
   i) determining a threshold intensity for image erasure;
   ii) measuring an initial image of a reference object;
   iii) determining which spatial regions of the image require further erasure according to the threshold intensity;
   iv) performing an erasure step on each spatial region requiring erasure using a fluence of photoexcitation radiation substantially less than a full-scale fluence of photoexcitation radiation;
   v) measuring a residual image;
   vi) repeating steps iii) to v) until all spatial regions no longer require further erasure;
   vii) generating calibration data by correlating a net fluence required for each spatial region with a corresponding intensity in the initial image.

14. A system for measuring x-ray images, said system comprising:
   a blocking-type photoconductive imaging device, the blocking-type photoconductive imaging device including a photoconductive layer and electrodes for applying a potential bias across the photoconductive layer, wherein an interface of the photoconductive layer is suitable for trapping photoexcited charges under application of the potential bias;
   a voltage source for applying a potential bias between said electrodes;
   an image readout device for interrogating the imaging device and obtaining an image having a spatial intensity or signal correlated with a spatial dependence of charges trapped at the interface of the photoconductive layer;
   a photoexcitation radiation source for generating photoexcitation radiation with a controlled spatial profile and with a wavelength suitable for photoexciting electron-hole pairs within the photoconductive layer; and
   a control and processing unit interfaced with at least the image readout device and the photoexcitation source, wherein the control and processing unit is configured to process a previously measured residual image to generate a prescribed spatial fluence profile for controlling the spatial profile of the photoexcitation radiation, such that the prescribed spatial fluence profile is spatially correlated with the previously measured residual image, and such that when the photoexcitation radiation is directed into the photoconductive layer with the prescribed spatial fluence profile, the photoexcitation radiation received at a given spatial location in the imaging detector is related to the intensity of the residual image at the given spatial location and a spatially-dependent concentration of electrons and holes are generated for locally reducing an effect of trapped charges located at or near an interface of the photoconductive layer.

15. The system according to claim 14 wherein said photoconductive layer includes a material selected from the group consisting of silicon, amorphous selenium, stabilized amorphous selenium, hydrogenated amorphous silicon (a-Si:H), gallium arsenide, cadmium telluride, cadmium zinc telluride (CZT), lead oxide (PbO), lead iodide (PbI2), mercury iodide (HgI2), and chalcogenide glass.

16. The system according to claim 14 wherein said imaging device is an x-ray light valve imaging device including an electro-optic modulator layer, wherein the electrodes are configured to apply a potential bias across said electro-optic modulator layer and said photoconductive layer, and wherein an electrode adjacent to said electro-optic modulator layer is optically transmissive.

17. The system according to claim 16 wherein the electro-optic modulator layer includes a liquid crystal.

18. The system according to claim 17 wherein said liquid crystal includes one of a nematic liquid crystal and a polymer dispersed liquid crystal.

19. The system according to claim 18 wherein said liquid crystal is a nematic liquid crystal that is selected from the group consisting of EMD E7 and ZL1-4792.

20. The system according to claim 14 wherein said photo-excitation radiation source is selected from the group consisting of a laser, a liquid crystal display, light emitting diodes, incandescent light, and fluorescent light.

* * * * *